United States Patent
Barbeyron et al.

(10) Patent No.: US 6,830,915 B2
(45) Date of Patent: Dec. 14, 2004

(54) GLYCOSYL HYDROLASE GENES AND THEIR USE FOR PRODUCING ENZYMES FOR THE BIODEGRADATION OF CARRAGEENANS

(75) Inventors: Tristan Barbeyron, Cleder (FR); Philippe Potin, Roscoff (FR); Christophe Richard, Plougourvest (FR); Bernard Henrissat, Uriage (FR); Jean-Claude Yvin, Saint Malo (FR); Bernard Kloareg, Saint Pol de Leon (FR)

(73) Assignee: Laboratoires Goemar, S.A., Saint Malo (FR)

( * ) Notice: Subject to any disclaimer, the term of this patent is extended or adjusted under 35 U.S.C. 154(b) by 0 days.

(21) Appl. No.: 09/988,200

(22) Filed: Nov. 19, 2001

(65) Prior Publication Data

US 2002/0094553 A1 Jul. 18, 2002

Related U.S. Application Data

(62) Division of application No. 09/269,731, filed as application No. PCT/FR97/01768 on Oct. 6, 1997, now Pat. No. 6,333,185.

(30) Foreign Application Priority Data

Oct. 7, 1996 (FR) .............................. 96 12204

(51) Int. Cl.[7] ................................................. C12N 9/24
(52) U.S. Cl. ....................................................... 435/200
(58) Field of Search ......................................... 435/200

(56) References Cited

PUBLICATIONS

Barbeyron, T, et al. (1994) Gene 139, 105–109.*
Potin, P. et al. (1991) Eur. J. Biochem. 201, 241–247.*
Potin, P. et al. (1995) Eur. J. Biochem. 228, 971–975.*

* cited by examiner

*Primary Examiner*—Charles L. Patterson, Jr.
(74) *Attorney, Agent, or Firm*—Dennison, Schultz, Dougherty & MacDonald

(57) ABSTRACT

The present invention relates to genes which code for glycosyl hydrolases having an HCA score with the iota-carrageenase of *Alteromonas fortis* which is greater than or equal to 65% over the domain extending between amino acids 164 and 311 of the protein sequence SEQ ID No. 2 of said iota-carrageenase, and to genes which code for glycosyl hydrolases having an HCA score with the kappa-carrageenase of *Alteromonas carrageenovora* which is greater than or equal to 75% over the domain extending between amino acids 117 and 262 of the protein sequence SEQ ID No. 6 of said kappa-carrageenase.

5 Claims, 4 Drawing Sheets

```
                                      ↓      ↓ ↓
 27          AVSPKTYKDADFYVAPTQQDVNY___DLVDDFGANGNDISD  64
             :         :    :        : ||  |  |  |||  |
 28         DTSEISEVPTELRAAASSFYTPPGQNVRANKKNLVIDYGVNHNDQND  74
     ↓
 65  DSNALQRAINAISRKPNGGTLLIPNGIYHFLGIQMKSNVHIRVESDVIEK  114
     | | :  | |  :  :   :|  |    :   :  | |||  :    :
 75  DSSKLNLAIKDLS__DTGGILTLPKGKYYLTKIRMRSNVHLEIEKGIVTY  122
                                                  ↓
115  PTWN GDGKNHRLFEVG__VNNIVRNFSFQGLGNGFLVDFKDSRDKNLAV  161
     | |     ||||  |          :  :  |  : |   | |     ||
123  PTKGLTPAKNHRIFDFASKTEEKIENASIVGKGGKFIVDLRGNSSKNQIV  172
                    ↓                            ↓
162  FKLGDVRNYKISNFTIDDNKTIFASILVDVTERNGRLHWSRNGIIERIKQ  211
       :    :  ||||||| | : ||  |: | :    :       ||||
173  ADVGNVINFKISNFTIKDEKTIFASILVSFIDKAGN_AWPHKGIIENIDQ  221
                    ↓           ↓↓
212  NNALFGYGLIQTYGADNILFRNLHSEGGIALRMETDNLLMKNYKQGGIRN  261
     | |  ||||||| | |||||| |:  ::  : | :: |||||  |  | |
222  ANAHIGYGLIQAYAADNILFNNLSCTGGVTLRLETDNLAMKIAKKGGVRD  271
                                                  ↓
262  IFADNIRCSKGLAAVMFGPHFMKNGDVQVINVSSVSCGSAVRSDSGFVEL  311
     |||    ||   |||   :::|||| |   ||    :      :   ||
272  IFATKIKNINGLTPVMFSPHFMENGKVTIDDVTAIGCAYAVRVEHGFIEI  321
      ↓
312  FSPIDEVHIRQSWKQAVESKLGRGCAQTPYARGNGGIRWAARVT___QKD  358
      |   |   ||   |   |||  |  | ||  | |   ||||
322  FDKGNRASA_DAFKNYIEGILGAGSVEVVYKRNNGRT_WAARIANDFNEA  369

359  ACLDKAKLEYGIEPGSFGTVKVFDVTARF_GYNADLKDQLDYFSTSNPM  407
     |   :  ||:|| | ||   : | :      ::    |  || |   |
370  AYNHSNPAVSGIKPGKFATSKVINVKATYKGTGAKLKQAFLSYLPCSER_  418
                                              ↓
408  CKRVCLPTKEQWSKQGQTYIGPSLAAVID_TTPEISKYDYDVKIFNVKRI  457
     : |||  :   :: ::        :    : ::      :    :
419  SK_VCRPGPDGFE_____YNGPSLGVTIDNTKRDNSLGNYNVNVSTSSVQ  462

457  NFPVNSHKTIDINIESSRVCNYY_GMSECSSSRWER           491
     || |      :    ||      |||     |
463  GFPNNYVLNVKYNI__PKVCNQNLG_SITSCN               491
```

FIG.1

```
  1 MKKPNFYGKMGRTALSSLFYLFFLGLVYGQQPTKTSNPNDQWTIKWSASDEFN_KNDPDW    59
    ||        |||       ||       |     |      ||||||
  1 MKPISIVAFPIPAISMLLLSAVSQAASM_QPPIAK_PGETWILQAKRSDEFNVK_DAT_    55

60 AKWIK_TGNLPNTSAWKWN_NQKNVKISNGIAELTM_RHNANNTPPDGGT_____YF__   108
    ||  |  |  | |||||  |  |||  ||  ||  |   | ||
 56 _KWNFQTENYGVWS_WK_NENAT_V__SNGKLKLTTKFESHQRTFWDGCNQQQVANYPLY   109

109 _TSGIFKSYQKFTYGYFEAKIQGADIGEGVCPSFWLYSDFDYSVAN_GETVYSEIDVVEL   166
     |||  ||      ||| || | ||     || || || ||  ||   |||||||||
110 YTSGVAKSPATGNYGYYEARIKGASTFPGVSPAFWMYSTIDRSLTKEGDVQYSEIDVVEL   169

167 QQFDWY_EGHQDDIYDMDLNLHAVVKENGQGVWKRPKMYPQEQLNKWRAM_DPSKDFHIY   224
                          ||| |       ||  ||          ||  ||| |
170 TQKSAVRES__DH__DLH_NI__VVK_NGKPTWMRPGSFPQTNHNGYHLPFDPRNDFHTY   221

225 GCEVNQNEIIWYVDGVE_VARKPNKYWHRPMNVTLSLGLRKPFVKFFDNKNNAINPETDA   283
    | |    | |.||| |  |  ||||  |  |||| ||| ||| |          | |
222 GVNVTKDKITWYVDG_EIVGEKDNLYWHRQMNLTLSQGLRAPHTQW___KCNQFYPSAN_   276

284 K_AREKLSDIPTSMYVDYVRVWEKSAGNTTNPPTSEVGTLKTKGSKLVIDHWDASTGTIS   342
    |||     |||. ||||| |  |  | |                |          |
277 KSA_EGF___PTSMEVDYVRTWVKVGNNNSAPGEGQSCPNTFVAVNSVQLSAAKQTLRKG   332

343 AVSNNTKTGQYAGSVNNASIAQIVTLKANTSYKVSAFGKASSPGTSAYLGISKASNNELI   402
                                 |   |.   ||
333 QSTTLESTVLPNCATNKKVIYSSSNKNVATVNSAGVV_KAKQNKGTATITVKTKQNKGKIDKL   392

403 SNFEFKTTSYSKGEIEIRTGNVQESYRIWYWSSGQAYCDDFNLVEINSGASQLNENETET   462

393 TIAVN                                                          397

463 ALEKGIHIYPNPYKNGPLTIDFGKPFSGEVQITGLNGRTFLRRNVVDQTSVQLLESKSKF   522

523 KSGLYIVKISGPDGEVSKKILVE                                       545
```

FIG.3

GLYCOSYL HYDROLASE GENES AND THEIR USE FOR PRODUCING ENZYMES FOR THE BIODEGRADATION OF CARRAGEENANS

CROSS-REFERENCE TO RELATED APPLICATIONS

This application is a division of application Ser. No. 09/269,731, filed Apr. 5, 1999, which is a 371 of PCT/FR97/01768, filed Oct. 6, 1997 now U.S. Pat. No. 6,333,185.

BACKGROUND OF THE INVENTION

The present invention relates to glycosyl hydrolase genes for the biotechnological production of oligosaccharides, especially sulfated oligo-carrageenans and more particularly oligo-iota-carrageenans and oligo-kappa-carrageenans, by the biodegradation of carrageenans.

The sulfated galactans of Rhodophyceae, such as agars and carrageenans, represent the major polysaccharides of Rhodophyceae and are very widely used as gelling agents or thickeners in various branches of activity, especially agri-foodstuffs. About 6000 tonnes of agars and 22,000 tonnes of carrageenans are extracted annually from red seaweeds for this purpose. Agars are commercially produced by red seaweeds of the genera *Gelidium* and *Gracilaria*. Carrageenans, on the other hand, are widely extracted from the genera *Chondrus*, *Gigartina* and *Eucheuma*.

Carrageenans consist of repeat D-galactose units alternately bonded by β1→4 and α1→3 linkages. Depending on the number and position of sulfate ester groups on the repeat disaccharide of the molecule, carrageenans are thus divided into several different types, namely: kappa-carrageenans, which possess one sulfate ester group, iota-carrageenans, which possess two sulfate ester groups, and lambda-carrageenans, which possess three sulfate ester groups.

The physicochemical properties and the uses of these polysaccharides as gelling agents are based on their capacity to undergo ball-helix conformational transitions as a function of the thermal and ionic environment [Kloareg et al., Oceanography and Marine Biology—An annual review 26: 259–315 (1988)].

Furthermore, carrageenans are structural analogs of the sulfated polysaccharides of the animal extracellular matrix (heparin, chondroitin, keratan, dermatan) and they exhibit biological activities which are related to certain functions of these glycosaminoglycans.

In particular, carrageenans are known:

(i)—for their action on the immune system, causing the secretion of interleukin or prostaglandins, (ii)—for their antiviral action on the AIDS virus HIV1, the herpes virus HSV1 and the hepatitis A virus, (iii)—as antagonists of the fixation of the growth factors of human cells, (iv)—and also for their action on the proliferation of keratinocytes and their action on the contractility of fibroblasts.

Furthermore, oligocarrageenans act on the adherence, the division and the protein synthesis of human cell cultures, doubtless as structural analogs of the glycosylated part of the proteins of the extracellular matrix. In plants, oligocarrageenans very significantly elicit enzymatic activities which are markers of growth (amylase) or of the phenolic defense metabolism (laminarinase, phenyl-alanineammonium lyase).

Carrageenans are extracted from red seaweeds by conventional processes such as hot aqueous extraction, and oligocarrageenans are obtained from carrageenans by chemical hydrolysis or, preferably, by enzymatic hydrolysis.

The production of oligocarrageenans by enzymatic hydrolysis generally comprises the following steps:

1) production of a glycosyl hydrolase by the culture of a marine bacterium;

2) enzymatic hydrolysis of the carrageenan with the glycosyl hydrolase thus obtained; and 3) fractionation and purification of the oligocarrageenans obtained.

Microorganisms which produce enzymes capable of hydrolyzing iota- and kappa-carrageenans were isolated by Bellion et al. in 1982 [Can. J. Microbiol. 28: 874–80 (1982)]. Some are specific for κ- or ι-carrageenan and others are capable of hydrolyzing both substrates. Another group of bacteria capable of degrading carrageenans was characterized by Sarwar et al. in 1983 [J. Gen. Appl. Microbiol. 29: 145–55 (1983)]. These yellow-orange bacteria are assigned to the *Cytophaga* group of bacteria and some of these bacteria have the property of hydrolyzing both agar and carrageenans.

Purification and characterisation of several ι-carrageenases and κ-carrageenases, such as the ι-carrageenase and κ-carrageenase of *Cytophaga drobachiensis*, the ι-carrageenase of *Alteromonas fortis* and the κ-carrageenase of *Alteromonas carrageenovora*, were described in the thesis of P. Potin ["Recherche, production, purification et caractérisation de galactane-hydrolases pour la préparation des parois d'algues rouges", (February 1992)]. A detailed study of the κ-carrageenase of *Alteromonas carrageenovora* was described by Potin et al. [Eur. J. Biochem. 228, 971–975 (1995)].

The availability of specific enzymes and tools for obtaining oligocarrageenans by genetic engineering could markedly improve their production.

SUMMARY OF THE INVENTION

The Applicant has now found novel glycosyl hydrolase genes which make it possible specifically to obtain either oligo-iota-carrageenans or oligo-kappa-carrageenans.

Thus the present invention relates to novel genes which code for glycosyl hydrolases having an HCA score with the iota-carrageenase of *Alteromonas fortis* which is greater than or equal to 65%, preferably greater than or equal to 70% and advantageously greater than or equal to 75% over the domain extending between amino acids 164 and 311 of the sequence [SEQ ID No. 2] of the iota-carrageenase of *Alteromonas fortis*.

The present invention relates more particularly to the nucleic acid sequence [SED ID No. 1] which codes for an iota-carrageenase as defined above, the amino acid sequence of which is the sequence [SEQ ID No. 2].

The present invention further relates to the genes which code for glycosyl hydrolases having an HCA score with the kappa-carrageenase of *Alteromonas carrageenovora* which is greater than or equal to 75%, preferably greater than 80% and advantageously greater than 85% over the domain extending between amino acids 117 and 262 of the sequence [SEQ ID No. 6] of the kappa-carrageenase of *Alteromonas carrageenovora*.

In particular, the invention relates to the nucleic acid sequence [SEQ ID No. 7] which codes for a kappa-carrageenase having a score as defined above, the amino acid sequence of which is the sequence [SEQ ID No. 8].

The glycosyl hydrolase genes of the invention are obtained by a process which consists in selecting proteins having an HCA score with the iota-carrageenase of *Alteromonas fortis* which is greater than or equal to 65%, preferably greater than or equal to 70% and advantageously greater than or equal to 75% over the domain extending between amino acids 164 and 311 of the sequence [SEQ ID No. 2] of the iota-carrageenase of *Alteromonas fortis*, and in sequencing the resulting genes by the conventional techniques well known to those skilled in the art.

The glycosyl hydrolase genes of the invention can also be obtained by a process which consists in selecting proteins having an HCA score with the kappa-carrageenase of *Alteromonas carrageenovora* which is greater than or equal to 75%, preferably greater than 80% and advantageously greater than 85% over the domain extending between amino acids 117 and 262 of the sequence [SEQ ID No. 6] of the kappa-carrageenase of *Alteromonas carrageenovora*, and in sequencing the resulting genes by the conventional techniques well known to those skilled in the art.

Finally, the present invention relates to the use of the above glycosyl hydrolase genes for obtaining, by genetic engineering, glycosyl hydrolases which are useful for the biotechnological production of oligocarrageenans.

The glycosyl hydrolases according to the invention are therefore characterized by the HCA score which they possess with a particular domain of the amino acid sequence of the iota-carrageenase of *Alteromonas fortis* or the kappa-carrageenase of *Alteromonas carrageenovora*.

The HCA or "Hydrophobic Cluster Analysis" method is a method of analyzing the sequences of proteins represented as a two-dimensional structure, which has been described by Gaboriaud et al. [FEBS Letters 224, 149–155 (1987)].

It is known that the three-dimensional structure of a protein governs its biological properties, the production of an active protein demanding correct folding.

It is also known that the primary structure of proteins varies much more substantially than the higher-order structures and that proteins can be grouped into families which show similar secondary and tertiary structures but sometimes have such divergent primary sequences that the mutual relationship between such proteins is not obvious. The code which relates primary structure and secondary structure therefore appears to be highly degenerate since very different primary structures can ultimately lead to similar secondary and tertiary structures [Structure 3, 853–859 (1995) and Proc. Natl. Acad. Sci. USA 92 (1995)].

The use of the HCA method has shown that the distribution, size and shape of these hydrophobic clusters along the amino acid sequences are representative of the 3D folding of the proteins studied.

Also, Woodcock et al. [Protein Eng. 5, 629–635 (1992)] have shown that the hydrophobic clusters defined by the α-helical 2D diagram are statistically centered on the regular secondary structures (α-helices, β-strands), that the 2D diagram based on the ax-helix carries the greatest amount of structural information and that the correspondence between hydrophobic clusters and elements of secondary structure is of the same quality for any type of folding (all α, all β, α/β and α+β), thus demonstrating that the HCA method can be used irrespective of the type of protein.

L. Lemesle-Varloot et al. [Biochimie 72, 555–574 (1990)] have shown that when two proteins have a similar distribution of hydrophobic clusters over a domain of at least 50 residues, their three-dimensional structures in this domain are considered to be superimposable and their functions to be analogous.

Thus, for example, Barbeyron et al. [Gene 139, 105–109 (1994)] used this HCA method for the comparison of the similarities in the shape, distribution and size of several hydrophobic clusters of the κ-carrageenase of *Alteromonas carrageenovora* with respect to enzymes from family 16 of glycosyl hydrolases.

The two-dimensional representation used in the HCA method is an α-helix in which the amino acids are arranged by computer processing to give 3.6 residues per turn. To obtain an easily readable plane image, the helix is cut in the longitudinal direction. Finally, to obtain the whole of the hydrophobic clusters situated at the edges of the image, the diagram is duplicated. The method uses a code which recognizes only two states: the hydrophobic state and the hydrophilic state.

The amino acids recognized as being hydrophobic are identified and grouped into characteristic geometric figures. Using these two states makes it possible to become independent of the tolerance shown by the two- and three-dimensional structures towards the variability of the primary sequences. Furthermore, this representation affords rapid observation of interactions over a short or medium distance since the first amino acid and the second, adjacent amino acid of a given residue are located on a segment of 17 amino acids. Finally, in contrast to the analytical methods based on the primary or secondary structures of proteins, no "window" of predefined length is used.

The fundamental characteristic of the α-helix representation is that, for a given globular protein or only a domain of this protein, the distribution of the hydrophobic residues on the diagram is not random. The hydrophobic residues (VILFWMY) form clusters of varying geometry and size. On the diagram, the hydrophilic and hydrophobic faces of the amphiphilic helices are very recognizable. Thus a horizontal diamond cluster corresponds to the hydrophobic face of an α-helix, the internal helices appear as large horizontal hydrophobic clusters and the β-strands appear as rather short, vertical hydrophobic clusters. The method makes it possible to identify the hydrophobic residues forming the core of the globular proteins and to locate the elements of secondary structure, namely the α-helices and the β-strands, independently of any knowledge of the secondary structure of the protein studied.

The HCA score between two proteins is calculated as follows:

For each cluster:

$$HCA\ score = 2CR/(RC_1 + RC_2) \times 100\%$$

where $RC_1$ and $RC_2$ are the number of hydrophobic residues in the cluster of protein 1 (cluster 1) and the cluster of protein 2 (cluster 2), respectively.

CR is the number of hydrophobic residues in the cluster 1 which correspond to the hydrophobic residues in the cluster 2.

The mean value obtained for all the clusters along the protein sequences compared gives the final HCA score.

On the HCA profiles, the amino acids are represented by their standard code of a single letter, with the exception of proline (P), glycine (G), serine (S) and threonine (T).

In fact, because of their particular properties, these residues are represented by the special symbols indicated below so as to facilitate their visual identification on the HCA diagrams (cf. list of abbreviations).

Proline introduces high constraints into the polypeptide chain and is considered systematically as an interruption in the clusters. In fact, proline residues stop or deform the helices and the lamellae. Glycine possesses a very substantial conformational flexibility because of the absence of a side chain in this amino acid. Serine and threonine are normally hydrophilic, but they can also be found in hydrophobic environments, such as α-helices, in which their hydroxyl group loses their hydrophilic character because of the hydrogen bond formed with the carbonyl group of the main chain. Within the hydrophobic β-lamellae, threonine is sometimes capable of replacing hydrophobic residues by virtue of the methyl group on its side chain.

Amino acids can be divided into four groups according to their hydrophobicity:
(i)—strongly hydrophobic residues: V, I, L and F;
(ii)—moderately hydrophobic residues: W, M and Y
→W appears at surface sites more frequently than F,
→M is encountered at various sites, internal or otherwise,
→Y can adapt to internal hydrophobic environments and is frequently found in loops;
(iii)—weakly hydrophobic residues: A and C are virtually insensitive to the hydrophobic character of their environment; and
(iv)—hydrophilic residues: D, E, N, Q, H, K and R.

Using this HCA method, the Applicant has found that proteins having an HCA score with the iota-carrageenase of *Alteromonas fortis* which is greater than or equal to 65% over the domain extending between amino acids 164 and 311 of said iota-carrageenase are enzymes of the glycosyl hydrolase type and more particularly iota-carrageenases appropriate for the production of oligo-iota-carrageenans from carrageenans.

The proteins having an HCA score which is greater than or equal to 70%, preferably greater than or equal to 75%, with the above domain 164–311 are particularly preferred for the purposes of the invention.

One particular example of glycosyl hydrolase obtained with a gene according to the invention is the protein having the amino acid sequence [SEQ ID No. 2], extracted from *Alteromonas fortis*.

Another particular example of glycosyl hydrolase obtained with a gene according to the invention is the protein having the amino acid sequence [SEQ ID No. 4], extracted from *Cytophaga drobachiensis*.

Likewise, the Applicant has found that proteins having an HCA score with the kappa-carrageenase of *Alteromonas carrageenovora* which is greater than or equal to 75% over the domain extending between amino acids 117 and 262 of said kappa-carrageenase are enzymes of the glycosyl hydrolase type and more particularly kappa-carrageenases appropriate for the production of oligo-kappa-carrageenans from carrageenans.

The proteins having an HCA score which is greater than or equal to 80%, preferably greater than or equal to 85%, with the above domain 117–262 are particularly preferred for the purposes of the invention.

The above proteins are advantageously extracted from marine bacteria.

One particular example of glycosyl hydrolase obtained with a gene according to the invention is the protein having the amino acid sequence [SEQ ID No. 6], extracted from *Alteromonas carrageenovora*.

Another particular example of glycosyl hydrolase obtained with a gene according to the invention is the protein having the amino acid sequence [SEQ ID No. 8], extracted from *Cytophaga drobachiensis*.

As indicated previously, the genes according to the invention, coding for glycosyl hydrolases, can be obtained by sequencing the genome of bacteria which product glycosyl hydrolases, as defined above, by the conventional methods well known to those skilled in the art.

The invention further relates to the expression vectors which carry the nucleic acid sequences according to the invention, with the means for their expression.

These expression vectors can be used to transform prokaryotic microorganisms, particularly *Escherichia coli*, or eukaryotic cells such as yeasts or fungi.

The invention will now be described in greater detail by means of the illustrative and non-limiting Examples below.

The methods used in these Examples are methods well known to those skilled in the art, which are described in detail in the work by Sambrook, Fristsch and Maniatis entitled "Molecular cloning: a laboratory manual", published in 1989 by Cold Spring Harbor Press, New York (2nd edition).

BRIEF DESCRIPTION OF THE DRAWINGS

The following description will be understood more clearly with the aid of FIGS. 1 to 4, which respectively show the following:

FIG. 1: The maximum similarity alignment, according to the method of Needleman and Wunsch [J. Mol. Biol. 48, 443–453 (1970)], of the amino acid sequence of the iota-carrageenase of *Alteromonas fortis* (SEQ ID NO: 2) (top part) and the iota-carrageenase of *C. drobachiensis* (SEQ ID NO: 4) (bottom part).

FIG. 3: The maximum similarity alignment, according to the method of Needleman and Wunsch, J. Mel. Biol. 48, 443–453 (1970), of the amino acid sequence of the kappa-carrageenase of *Alteromonas carrageenovora* (SEQ ID NO: 6) (top part) and *Cytophaga drobachiensis* (SEQ ID NO: 8) (bottom part).

Figure 2:
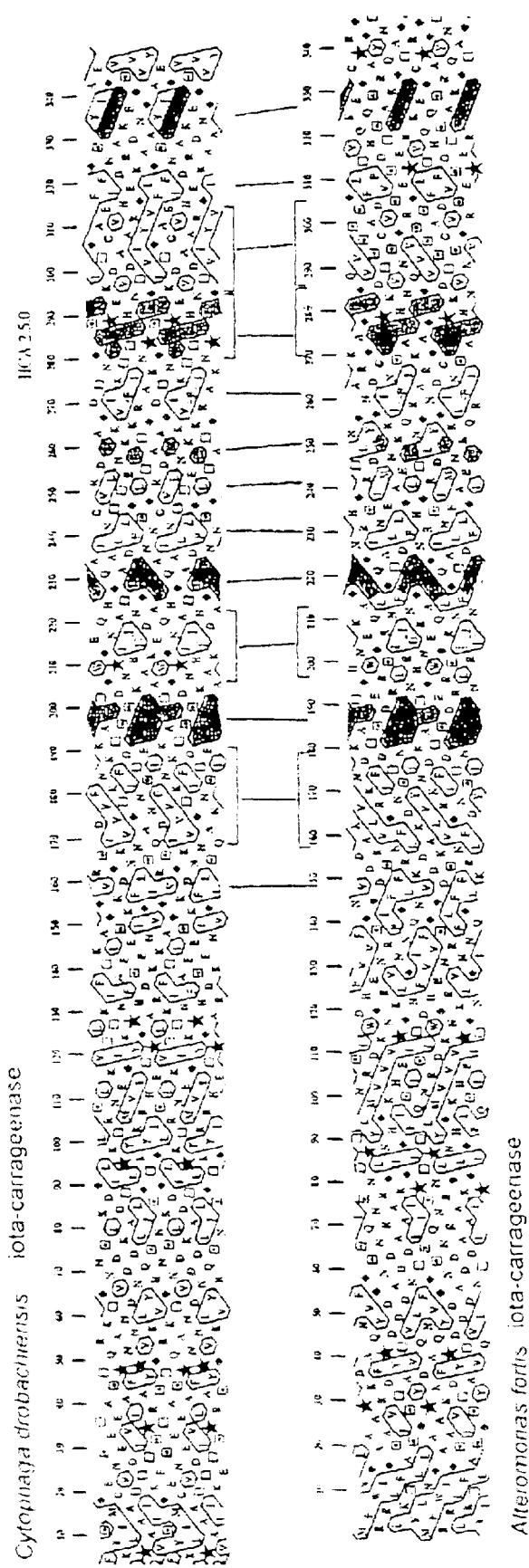
FIG. 2: The HCA profiles of the amino acid sequences of the iota-carrageenases of *Cytophaga drobachiensis* and *Alteromonas fortis*.

The abbreviations or special symbols used for the amino acids in the Examples below are as follows:

Glycine: ◇
Proline: *
Threonine:☐
Sérine:▣
Alanine: A
Valine: V
Leucine: L
Isoleucine: I
Methionine: M
Phenylalanine: F
Tryptophan: W
Cysteine: C
Asparagine: N
Glutamine: Q
Tyrosine: Y
Aspartate: D
Glutamate: E
Lysine: K
Arginine: R
Histidine: H

EXAMPLE 1

The iota-carrageenases of *Cytophaga drobachiensis* and *Alteromonas fortis*

SECTION 1: Cloning of the Genes of the Iota-Carrageenases of *Cytophaga drobachiensis* and *Alteromonas fortis*

*Cytophaga drobachiensis* was isolated by the Applicant from the red seaweed *Delesseria sanguinea* [Eur. J. Biochem. 201 : 241–247 (1991)]. *Alteromonas fortis* (ATCC 43554) was obtained from the American Type Culture Collection. The strains were cultivated on a Zobell medium at 25° C.

Genome libraries of the DNAs of *C. drobachiensis* and *A. fortis* were constructed.

The strain used to construct these libraries, namely *Escherichia coli* DH5α (Rec A, endA1, gyrA96, thi1, hsdR17 [rk– mk+], supE44, relA1, lacZΔM15), was cultivated on Luria-Bertani medium (LB medium) at 37° C. or on a so-called Zd medium (bactotryptone 5 g/l, yeast extract 1 g/l, NaCl 10 g/l; pH=7.2) at 22° C., to which 2% of κ-carrageenan were added.

Ampicillin (50 μg/ml) or tetracycline (15 μg/ml) was added to the agar or non-agar culture media from stock solutions prepared in 50% ethanol (to avoid solidification at the storage temperature, –20° C.), except in the case of the non-recombinant strain DH5α.

The expression vector used is plasmid pAT153 described in Nature 283: 216 (1980). This plasmid contains two antibiotic resistance genes: a tetracycline resistance gene and a gene which codes for a β-lactamase, an enzyme of the cytoplasmic membrane which degrades ampicillin.

The total DNA of *C. Drobachiensis* and the total DNA of *A. fortis* were prepared by the method described by Barbeyron et al. [J. Bacteriol. 160, 586–590 (1984)].

The genomic DNAs of *C. drobachiensis* and *A. fortis* were cleaved with the restriction endonucleases NdeII and Sau3AI respectively. In fact, in the case of *C. drobachiensis*, the restriction endonuclease NdeII was used preferentially because the DNA of this bacterium is methylated on the C residue of the GATC sequence.

The purified DNA fragments of 5000 to 10,000 bp were cloned at the BamHI site of plasmid pAT153, which cleaves the tetracycline resistance gene.

6000 clones were obtained in each of the genome libraries.

The five positive *C. drobachiensis* clones and the two positive *A. fortis* clones, which hollowed out a hole in the ι-carrageenan after one week of culture at 22° C, are referred to respectively as pIC1 to pIC5 and pIP1 to pIP2.

1. Cloning from *C. drobachiensis*

The cloning of this gene is described in detail by T. Barbeyron in the doctoral thesis examined on Oct. 28, 1993 at the Université Pierre et Marie Curie, Roscoff.

The plasmid DNA was isolated from the above five clones by the alkaline lysis method [Nucleic Acid Res. 7: 1513 (1979)].

The sizes and mapping of the inserts showing an ι-carrageenase activity were determined by agarose gel electrophoresis after single and double digestion of their plasmids with various restriction enzymes.

The DNA fragments were extracted from the agarose by the glass wool method.

All the plasmids obtained contain an identical PvuII fragment of 3.3 kb.

This fragment was subcloned in phagemid pbluescript KSII (Stratagene) (pICP07 and pICP16).

Likewise, the internal NdeI fragment and a HindIII fragment partially comprising the PvuII fragment were subcloned to give the pICN22 and pICH42 subclones, respectively.

To locate the ι-carrageenase gene, libraries were constructed from the pICP07 and pICP16 subclones in phagemid pbluescript with the aid of the exonuclease III of *E. coli*, using the "ExoIII" kit from Pharmacia.

The subclones and the ExoIII clones obtained were plated onto Zd medium solidified with ι-carrageenan.

Only the pICP16 and pICP07 clones and the ExoIII pICP074 and pICP0712 clones (obtained by degradation with ExoIII for 4 minutes and 12 minutes, respectively, from the pICP07 clone) are ι-carrageenase-positive.

2. Cloning from *Alteromonas fortis*

The DNA of the pIP1 and pIP2 clones showed inserts of 10.45 kb and 4.125 kb respectively, having a common fragment of 3 kb. These clones showed a positive ι-carrageenase activity. Different fragments were subcloned and plated as described above. However, none of the subclones obtained proved to be ι-carrageenase-positive.

SECTION 2: Determination of the Nucleotide Sequences of the Genes Coding for the ι-carrageenases of *Cytophaga drobachiensis* and *Alteromonas fortis*

1. Sequence of the *Cytophaga drobachiensis* Gene

Plasmid pICP0712 was used to determine the nucleotide sequence of the gene responsible for the ι-carrageenase activity of *C. drobachiensis* [SEQ ID No. 3].

This nucleotide sequence is composed of 1837 bp. Translation of the six reading frames revealed only one open frame, called cgiA. The potential initiation codon is situated 333 bp beyond the 5'P end of the sequence.

The protein sequence [SEQ ID No. 4] deduced from the sequence of cgiA is composed of 391 amino acids, corresponding to a theoretical molecular weight of 53.4 kDa. The hydropathic profile of this protein shows a hydrophobic region covering the first 24 amino acids. The presence of a positively charged amino acid (Lys) followed by a hydrophobic block and then by a polar segment of six amino acids suggests that this domain could be a signal peptide. According to the analyses performed by the method of Von Heijne [J. Mol. Biol. 184: 99–105 (1985)], the signal peptidase would cleave between valine (Val$^{24}$) and threonine (Thr$^{25}$). The mature protein devoid of its signal peptide would have a theoretical molecular weight of 50.7 kDa. The identity of the cgiA gene was confirmed by determination of the amino acids at the NH$_2$ end of the partially purified protein. The sequence obtained matches the one deduced from the nucleotide sequence. The first amino acid is situated 14 residues from the NH$_2$ end generated by the signal peptidase. As the presence of the two prolines following the amino acids determined by microsequencing had slightly disturbed the order of appearance of the N-terminal residues, the sequence of an internal oligopeptide, purified by HPLC after cleavage with trypsin, was established. The sequence NH$_2$ATYKCOOH obtained is situated near the C-terminal end of the iotase (residues 396 to 399).

2. Sequence of the *Alteromonas fortis* Gene

Plasmids pIHP15 and pIHPX17, subcloned from pIP1 and pIP2, were used to determine the nucleotide sequence of the gene responsible for the ι-carrageenase activity of *Alteromonas fortis*, SEQ ID No. 1. The 2085 bp fragment contains a single open reading frame of 1473 bp, called cgiA. The sequence situated upstream of the initiation codon (ATG$^{211}$) is not a coding sequence.

The protein sequence deduced from the sequence of the *A. fortis* ι-carrageenase gene [SEQ ID No. 2] consists of 491 amino acids, corresponding to a theoretical molecular weight of 54.802 kDa. In the present case, again, the N-terminal part of the protein exhibits a high hydrophobicity, suggesting that this domain could be a signal peptide; the hypothetical cleavage site would be situated between glycine (Gly$^{26}$) and alanine (Ala$^{27}$). The mature protein devoid of its signal peptide would have a theoretical molecular weight of 51.95 kDa, corresponding to a value similar to the molecular weight obtained with the protein purified by SDS-PAGE, namely 57 kDa.

SECTION 3: Comparison of the Protein Sequences of the ι-Carrageenases of *Cytophaga drobachiensis* and *Alteromonas fortis*

After removal of the signal peptide from each sequence, it could be seen that the sequence of the ι-carrageenase of *C. drobachiensis* has similarities to that of the ι-carrageenase of *A. fortis*.

In fact, the two sequences of iota-carrageenase have a similarity of 43.2% over the whole of the linear sequence alignment. This similarity is particularly high (57.8%) between amino acids 164 and 311 (numbering of the iota-carrageenase of *Alteromonas fortis* (FIG. 1)).

At the same time, an HCA analysis showed that the HCA score between the two proteins is 82% over a domain of 293 amino acids and reaches 90.5% in the case of said domain 164–311 (FIG. 2).

No significant similarity to other polysaccharidases known hitherto could be demonstrated.

These two enzymes therefore constitute a novel family of glycosyl hydrolases.

EXAMPLE II

The Kappa-Carrageenases of *Alteromonas carrageenovora* and *Cytophaga drobachiensis*

SECTION 1: Cloning of the Kappa-Carrageenase Genes

*Alteromonas carrageenovora* ATCC 43555 was obtained from the American Type Culture Collection. The strains *A. carrageenovora* and *C. drobachiensis* were cultivated under conditions identical to those mentioned in section 1 of Example I.

Likewise, genome libraries were constructed using the strain *Escherichia coli* DH5α and plasmid vector pAT153.

1. Cloning from *Alteromonas carrageenovora*

The preparation of this gene is described in detail by T. Barbeyron in the thesis cited above (cf. Example 1) and in Gene 139, 105–109 (1994).

From the genome library of *Alteromonas carrageenova*, 4 *E. coli* clones, called K1 to K4, were capable of hydrolyzing kappa-carrageenan.

Plasmids pKA1 to pKA4 were purified from the four independent clones and mapped with the aid of the restriction endonucleases BamHI, DraI, EcoRI, HindIII, MluI, PstI, PvuII, SalI, SspI, XbaI and XhoI.

The presence of a 2.2 kb DraI-HindIII fragment was noted in each plasmid.

This common fragment, which is the whole insert of plasmid pKA3, was sequenced in its entirety from plasmid pKA3.

2. Cloning from *Cytophaga drobachiensis*

From the genome library of *C. drobachiensis*, five *E. coli* clones, called pKC1 to pKC5, were capable of hollowing out a hole in the substrate. The plasmids isolated and purified from said clones were mapped with restriction endonucleases.

Internal fragments of 1100 bp and 600 bp respectively were subcloned from pKC1 in phagemid pbluescript and were called pKCE11 and pKCN6.

Plasmids pKC1, pKCE11 and pKCN6 were used to determine the nucleotide sequence of the kappa-carrageenase gene.

SECTION 2: Determination of the Sequences of the Genes Coding for the Kappa-Carrageenases of *Alteromonas carrageenovora* and *Cytophaga drobachiensis*

1. Sequence of the *Alteromonas carrageenovora* Gene

The number of nucleotides in the pKA3 insert is 2180 bp. Translation in the six reading frames reveals the presence of three open frames, only one of which is complete; this one separates the other two, which are only partial. All three of them are located on the same DNA strand. The second open frame, called cgkA, read in the third reading frame, contains 1191 bp [SEQ ID No. 5].

The translation product of the cgkA gene corresponds to a protein of 397 amino acids with a theoretical molecular weight of 44,212 Da (SEQ ID No. 6). The hydropathic profile of this protein shows a highly hydrophobic domain, extending over 25 amino acids, at the N-terminal end. This domain comprises a positively charged amino acid (Lys) followed by a segment rich in hydrophobic amino acids and then by three polar amino acids. These results suggest that a signal peptide is involved. The N-terminal sequence of the protein purified from the culture supernatant was determined, thereby confirming the identity of the gene. These results indicate that the signal peptidase cleaves the protein between residues 25 and 26, which is consistent with Von Heijne's rule (−3, −1). The mature protein therefore has a theoretical molecular weight of 41.6 kDa.

2. Sequence of the *Cytophaga drobachiensis* Gene

The pKC1 insert of 4425 bp contains a single open reading frame of 1635 bp, called cgkA (SEQ ID No. 7).

The protein translated from the kappa-carrageenase gene is a protein comprising 545 amino acids with a molecular weight of 61.466 kDa [SEQ ID No. 8].

The hydropathic profile of this protein shows a highly hydrophobic domain at the N-terminal end, suggesting that a signal peptide is involved.

According to Von Heijne's rule (−3, −1), the cleavage site of the signal peptidase should be situated between threonine and serine in positions 35 and 36 respectively, with the codon ATG$^{875}$ as the initiation codon.

The molecular weight of the protein, calculated after removal of the signal peptide, is 57.4 kDa, which is greater than the molecular weight determined for the purified extracellular κ-carrageenase, namely 40.0 kDa.

SECTION 3: Comparison of the Protein Sequences of the κ-carrageenases of *Alteromonas carrageenovora* and *Cytophaga drobachiensis*

The κ-carrageenase of *C. drobachiensis* has a similarity of 36.1% with the κ-carrageenase of *Alteromonas carrageenovora* over the whole of the linear sequence alignment.

This similarity is particularly high between amino acids 117 and 262 (51.8%) (numbering of the κ-carrageenase of *Alteromonas carrageenovora*) (FIG. 3).

Figure 4:
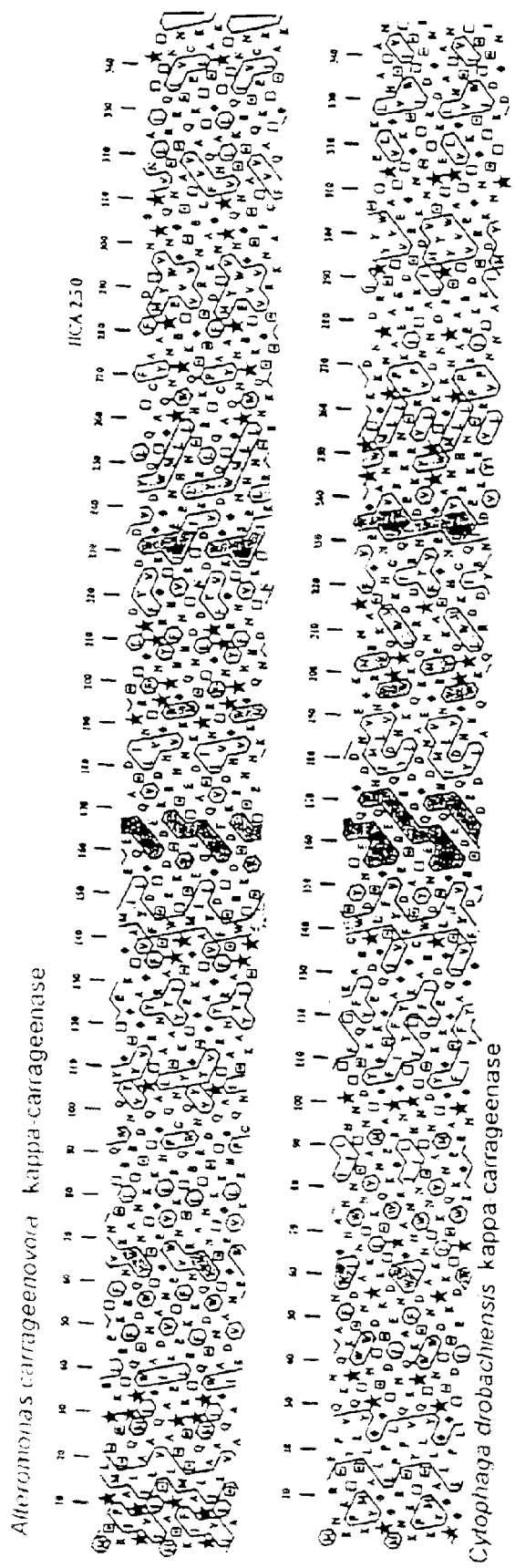
FIG. 4: The HCA profiles of the amino acid sequences of the kappa-carrageenases of *Cytophaga drobachiensis* and *Alteromonas fortis*.

As previously, this similarity is substantiated by HCA analysis, which shows an HCA score between the two proteins of 75.4% over said domain of 145 amino acids (FIG. 4).

HCA analysis also shows that these two proteins belong to family 16 of glycosyl hydrolases, which includes endoxyglucan transferases (XET), laminarinases, lichenases and agarases. In fact, the HCA score of the two kappa-carrageenases is 67.5% with XET, 67.6% with laminarinases, 73.7% with lichenases and 71.5% with agarases.

What is claimed is:

1. An isolated protein having glycosyl hydrolase activity, said protein being selected from the group consisting of
   (a) a protein comprising an amino acid sequence depicted in SEQ ID NO: 2;
   (b) a protein encoded by the nucleotide sequence of SEQ ID NO: 1;
   (c) a protein having a hydrophobic cluster analysis (HCA) score with the iota-carrageenase of *Alteromonas fortis* which is greater than or equal to 65% over the domain extending between amino acids 164 and 311 of the amino acid sequence of *Alteromonas fortis* that is SEQ ID NO: 2.

2. A protein according to claim 1, wherein the HCA score is greater than or equal to 70%.

3. A protein according to claim 1, wherein the HCA score is greater than or equal to 75%.

4. A protein according o claim 1, comprising an amino acid sequence depicted in SEQ ID NO: 2, wherein the protein is extracted from *Alteromonas fortis*.

5. A method of producing iota-carrageenans, comprising
   (a) genetically modifying a host cell with a nucleic acid molecule having SEQ ID NO: 1, or with a vector comprising a nucleic acid molecule having SEQ ID NO: 1;
   (b) culturing the host cell until a protein having glycosyl hydrolase activity is produced;
   (c) isolating the protein having glycosyl hydrolase activity;
   (d) contacting the isolated protein having glycosyl hydrolase activity with a carrageenan until iota-carrageenans are produced; and
   (e) recovering the iota-carrageenans.

* * * * *

SEQUENCE LISTING (1) GENERAL INFORMATION:

(iii) NUMBER OF SEQUENCES: 8

(2) INFORMATION FOR SEQ ID NO: 1:

(i) SEQUENCE CHARACTERISTICS:
      (A) LENGTH: 2085 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (ix) FEATURE:
      (A) NAME/KEY: CDS
      (B) LOCATION:join(211..1683, 1880..2083)

(xi) SEQUENCE DESCRIPTION: SEQ ID NO: 1:

```
AAGCTTTCCG ATTCTATCAT CGAAGTCATA GGAGTGGGTA AACAAAAAAG CATGAAACTA      60

GCTTTTTAAA ATACAGACTT TCAATATAGG TCGCACACAA TATTAACGAA TAAATAAGCA     120

AATCATATAC ATAATCATTG CTTTAAATAT GTTTTAATAC AGATATAAAC ATAGTATGTT     180

TGTGTTTTTG GTATCTATCG GAGTGAAAAC ATG CGC TTA TAT TTT AGA AAG TTG     234
                                 Met Arg Leu Tyr Phe Arg Lys Leu
                                  1               5

TGG TTA ACA AAT TTA TTT TTA GGC GGA GCA CTG GCC TCT TCA GCT GCG     282
Trp Leu Thr Asn Leu Phe Leu Gly Gly Ala Leu Ala Ser Ser Ala Ala
         10                  15                  20

ATA GGG GCT GTC TCC CCC AAG ACT TAT AAG GAC GCA GAT TTT TAT GTT     330
Ile Gly Ala Val Ser Pro Lys Thr Tyr Lys Asp Ala Asp Phe Tyr Val
 25                  30                  35                  40

GCC CCT ACT CAA CAA GAT GTT AAC TAT GAT TTA GTT GAT GAT TTT GGC     378
Ala Pro Thr Gln Gln Asp Val Asn Tyr Asp Leu Val Asp Asp Phe Gly
                 45                  50                  55

GCT AAT GGA AAC GAC ACT AGT GAT GAC AGT AAT GCT TTA CAA AGA GCA     426
Ala Asn Gly Asn Asp Thr Ser Asp Asp Ser Asn Ala Leu Gln Arg Ala
             60                  65                  70

ATT AAT GCT ATT AGT AGA AAA CCG AAT GGG GGC ACT TTA CTA ATA CCG     474
Ile Asn Ala Ile Ser Arg Lys Pro Asn Gly Gly Thr Leu Leu Ile Pro
         75                  80                  85

AAT GGA ACT TAC CAT TTC CTC GGC ATA CAG ATG AAG TCG AAC GTA CAC     522
Asn Gly Thr Tyr His Phe Leu Gly Ile Gln Met Lys Ser Asn Val His
 90                  95                 100

ATC CGT GTT GAG AGT GAC GTG ATA ATC AAG CCA ACG TGG AAT GGG GAT     570
Ile Arg Val Glu Ser Asp Val Ile Ile Lys Pro Thr Trp Asn Gly Asp
105                 110                 115                 120

GGC AAA AAC CAC CGA CTA TTT GAA GTT GGC GTA AAC AAT ATT GTA AGA     618
Gly Lys Asn His Arg Leu Phe Glu Val Gly Val Asn Asn Ile Val Arg
                125                 130                 135

AAC TTC AGC TTT CAA GGG TTA GGA AAC GGT TTT TTG GTG GAT TTT AAA     666
Asn Phe Ser Phe Gln Gly Leu Gly Asn Gly Phe Leu Val Asp Phe Lys
            140                 145                 150

GAT TCT CGC GAC AAA AAC TTA GCT GTT TTT AAG TTA GGC GAT GTT AGA     714
Asp Ser Arg Asp Lys Asn Leu Ala Val Phe Lys Leu Gly Asp Val Arg
        155                 160                 165

AAT TAC AAA ATT TCC AAT TTT ACC ATT GAT GAT AAT AAA ACG ATA TTT     762
Asn Tyr Lys Ile Ser Asn Phe Thr Ile Asp Asp Asn Lys Thr Ile Phe
    170                 175                 180
```

-continued

| | |
|---|---|
| GCC TCA ATT TTA GTG GAC GTA ACA GAA CGT AAT GGG CGG TTA CAT TGG<br>Ala Ser Ile Leu Val Asp Val Thr Glu Arg Asn Gly Arg Leu His Trp<br>185                        190                        195                        200 | 810 |
| TCG CGT AAT GGA ATT ATC GAA AGA ATA AAA CAA AAT AAC GCT TTG TTC<br>Ser Arg Asn Gly Ile Ile Glu Arg Ile Lys Gln Asn Asn Ala Leu Phe<br>                       205                        210                        215 | 858 |
| GGC TAC GGC CTT ATT CAA ACC TAT GGC GCA GAT AAT ATT TTG TTT AGG<br>Gly Tyr Gly Leu Ile Gln Thr Tyr Gly Ala Asp Asn Ile Leu Phe Arg<br>220                        225                        230 | 906 |
| AAC CTC CAT TCG GAA GGC GGA ATT GCG TTA CGG ATG GAA ACT GAC AAC<br>Asn Leu His Ser Glu Gly Gly Ile Ala Leu Arg Met Glu Thr Asp Asn<br>                 235                        240                        245 | 954 |
| TTA CTT ATG AAA AAT TAT AAG CAA GGC GGA ATA AGA AAC ATC TTT GCT<br>Leu Leu Met Lys Asn Tyr Lys Gln Gly Gly Ile Arg Asn Ile Phe Ala<br>250                        255                        260 | 1002 |
| GAT AAT ATC AGA TGT AGC AAA GGA CTT GCG GCG GTC ATG TTT GGC CCA<br>Asp Asn Ile Arg Cys Ser Lys Gly Leu Ala Ala Val Met Phe Gly Pro<br>265                        270                        275                        280 | 1050 |
| CAT TTT ATG AAG AAT GGA GAT GTG CAA GTG ACC AAT GTC AGC TCA GTT<br>His Phe Met Lys Asn Gly Asp Val Gln Val Thr Asn Val Ser Ser Val<br>                 285                        290                        295 | 1098 |
| AGT TGC GGT TCG GCT GTA CGA AGT GAT AGT GGA TTT GTC GAA CTC TTT<br>Ser Cys Gly Ser Ala Val Arg Ser Asp Ser Gly Phe Val Glu Leu Phe<br>                       300                        305                        310 | 1146 |
| AGC CCG ACA GAC GAA GTA CAT ACG CGT CAA AGT TGG AAA CAA GCC GTT<br>Ser Pro Thr Asp Glu Val His Thr Arg Gln Ser Trp Lys Gln Ala Val<br>                 315                        320                        325 | 1194 |
| GAA AGT AAA TTG GGC CGA GGG TGT GCG CAA ACC CCT TAT GCT AGA GGT<br>Glu Ser Lys Leu Gly Arg Gly Cys Ala Gln Thr Pro Tyr Ala Arg Gly<br>330                        335                        340 | 1242 |
| AAT GGT GGT ACA CGG TGG GCG GCT CGC GTA ACA CAA AAA GAC GCG TGT<br>Asn Gly Gly Thr Arg Trp Ala Ala Arg Val Thr Gln Lys Asp Ala Cys<br>345                        350                        355                        360 | 1290 |
| TTA GAT AAA GCA AAA CTG GAA TAT GGA ATA GAG CCT GGT TCA TTT GGC<br>Leu Asp Lys Ala Lys Leu Glu Tyr Gly Ile Glu Pro Gly Ser Phe Gly<br>                 365                        370                        375 | 1338 |
| ACG GTT AAA GTC TTT GAT GTT ACA GCG CGT TTT GGT TAT AAC GCA GAT<br>Thr Val Lys Val Phe Asp Val Thr Ala Arg Phe Gly Tyr Asn Ala Asp<br>                       380                        385                        390 | 1386 |
| CTT AAA CAG GAC CAG CTA GAC TAC TTT TCT ACA TCC AAC CCT ATG TGC<br>Leu Lys Gln Asp Gln Leu Asp Tyr Phe Ser Thr Ser Asn Pro Met Cys<br>                 395                        400                        405 | 1434 |
| AAG CGT GTA TGC CTT CCT ACA AAA GAA CAA TGG AGT AAG CAA GGC CAA<br>Lys Arg Val Cys Leu Pro Thr Lys Glu Gln Trp Ser Lys Gln Gly Gln<br>410                        415                        420 | 1482 |
| ATT TAC ATT GGT CCG TCA TTA GCT GCA GTA ATT GAT ACC ACA CCT GAA<br>Ile Tyr Ile Gly Pro Ser Leu Ala Ala Val Ile Asp Thr Thr Pro Glu<br>425                        430                        435                        440 | 1530 |
| ACT TCA AAA TAC GAT TAT GAT GTG AAA ACT TTT AAC GTC AAA AGA ATA<br>Thr Ser Lys Tyr Asp Tyr Asp Val Lys Thr Phe Asn Val Lys Arg Ile<br>                 445                        450                        455 | 1578 |
| AAT TTT CCT GTA AAT TCA CAC AAG ACT ATC GAC ACG AAT ACT GAA AGT<br>Asn Phe Pro Val Asn Ser His Lys Thr Ile Asp Thr Asn Thr Glu Ser<br>                 460                        465                        470 | 1626 |
| AGC CGT GTC TGC AAT TAT TAC GGT ATG TCC GAA TGC TCC AGC AGT CGA<br>Ser Arg Val Cys Asn Tyr Tyr Gly Met Ser Glu Cys Ser Ser Ser Arg<br>                 475                        480                        485 | 1674 |
| TGG GAG CGA TAGATTAAGC CGCTATATTC ATTTACTAGG TAAAACTTCA<br>Trp Glu Arg | 1723 |

-continued

```
       490
AGCCGCATTC GAAGAACTAT CGAACGCGGC TTTTTTGTTA AGAGCGCCTA TGACTCAGTA      1783

TATTTTGTAT AAATATAATT TTACATCTTG TTAAAGTAAA CATCATATGT TTATATAGGT      1843

GCAATCTAAT TTGTTAATAT AGTGTTGGAG ATAGGT ATG AAA GGT GTT TCT ACG        1897
                                        Met Lys Gly Val Ser Thr
                                                        495

AAA AAT GCT CTT TTA TTT GCA GGC TTT TCG TTA AGT CTA GTT GCA CAG         1945
Lys Asn Ala Leu Leu Phe Ala Gly Phe Ser Leu Ser Leu Val Ala Gln
            500                 505                 510

TCA GTT AGT GCA CAA GAA GCA AAA CAG CCT GAA AAA GAA GAA AAA GAT         1993
Ser Val Ser Ala Gln Glu Ala Lys Gln Pro Glu Lys Glu Glu Lys Asp
515                 520                 525

GTT GAG GTG ATT TTG GTA TCG GCA CAA AAG CGT GAG CAA GCG CTT AAA         2041
Val Glu Val Ile Leu Val Ser Ala Gln Lys Arg Glu Gln Ala Leu Lys
530                 535                 540                 545

GAA GTG CCT GTA TCA ATT GAA GTT ATT CAA GGC GAC CTT CTA GA              2085
Glu Val Pro Val Ser Ile Glu Val Ile Gln Gly Asp Leu Leu
                550                 555
```

(2) INFORMATION FOR SEQ ID NO: 2:

(i) SEQUENCE CHARACTERISTICS:
        (A) LENGTH: 559 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Arg Leu Tyr Phe Arg Lys Leu Trp Leu Thr Asn Leu Phe Leu Gly
1               5                   10                  15

Gly Ala Leu Ala Ser Ser Ala Ala Ile Gly Ala Val Ser Pro Lys Thr
                20                  25                  30

Tyr Lys Asp Ala Asp Phe Tyr Val Ala Pro Thr Gln Gln Asp Val Asn
            35                  40                  45

Tyr Asp Leu Val Asp Asp Phe Gly Ala Asn Gly Asn Asp Thr Ser Asp
        50                  55                  60

Asp Ser Asn Ala Leu Gln Arg Ala Ile Asn Ala Ile Ser Arg Lys Pro
65                  70                  75                  80

Asn Gly Gly Thr Leu Leu Ile Pro Asn Gly Thr Tyr His Phe Leu Gly
                85                  90                  95

Ile Gln Met Lys Ser Asn Val His Ile Arg Val Glu Ser Asp Val Ile
            100                 105                 110

Ile Lys Pro Thr Trp Asn Gly Asp Gly Lys Asn His Arg Leu Phe Glu
        115                 120                 125

Val Gly Val Asn Asn Ile Val Arg Asn Phe Ser Phe Gln Gly Leu Gly
    130                 135                 140

Asn Gly Phe Leu Val Asp Phe Lys Asp Ser Arg Asp Lys Asn Leu Ala
145                 150                 155                 160

Val Phe Lys Leu Gly Asp Val Arg Asn Tyr Lys Ile Ser Asn Phe Thr
                165                 170                 175

Ile Asp Asp Asn Lys Thr Ile Phe Ala Ser Ile Leu Val Asp Val Thr
            180                 185                 190

Glu Arg Asn Gly Arg Leu His Trp Ser Arg Asn Gly Ile Ile Glu Arg
        195                 200                 205

Ile Lys Gln Asn Asn Ala Leu Phe Gly Tyr Gly Leu Ile Gln Thr Tyr
    210                 215                 220
```

```
Gly Ala Asp Asn Ile Leu Phe Arg Asn Leu His Ser Glu Gly Gly Ile
225                 230                 235                 240

Ala Leu Arg Met Glu Thr Asp Asn Leu Leu Met Lys Asn Tyr Lys Gln
            245                 250                 255

Gly Gly Ile Arg Asn Ile Phe Ala Asp Asn Ile Arg Cys Ser Lys Gly
            260                 265                 270

Leu Ala Ala Val Met Phe Gly Pro His Phe Met Lys Asn Gly Asp Val
            275                 280                 285

Gln Val Thr Asn Val Ser Ser Val Ser Cys Gly Ser Ala Val Arg Ser
290                 295                 300

Asp Ser Gly Phe Val Glu Leu Phe Ser Pro Thr Asp Glu Val His Thr
305                 310                 315                 320

Arg Gln Ser Trp Lys Gln Ala Val Glu Ser Lys Leu Gly Arg Gly Cys
            325                 330                 335

Ala Gln Thr Pro Tyr Ala Arg Gly Asn Gly Gly Thr Arg Trp Ala Ala
            340                 345                 350

Arg Val Thr Gln Lys Asp Ala Cys Leu Asp Lys Ala Lys Leu Glu Tyr
355                 360                 365

Gly Ile Glu Pro Gly Ser Phe Gly Thr Val Lys Val Phe Asp Val Thr
370                 375                 380

Ala Arg Phe Gly Tyr Asn Ala Asp Leu Lys Gln Asp Gln Leu Asp Tyr
385                 390                 395                 400

Phe Ser Thr Ser Asn Pro Met Cys Lys Arg Val Cys Leu Pro Thr Lys
            405                 410                 415

Glu Gln Trp Ser Lys Gln Gly Gln Ile Tyr Ile Gly Pro Ser Leu Ala
            420                 425                 430

Ala Val Ile Asp Thr Thr Pro Glu Thr Ser Lys Tyr Asp Tyr Asp Val
            435                 440                 445

Lys Thr Phe Asn Val Lys Arg Ile Asn Phe Pro Val Asn Ser His Lys
450                 455                 460

Thr Ile Asp Thr Asn Thr Glu Ser Ser Arg Val Cys Asn Tyr Tyr Gly
465                 470                 475                 480

Met Ser Glu Cys Ser Ser Ser Arg Trp Glu Arg Met Lys Gly Val Ser
            485                 490                 495

Thr Lys Asn Ala Leu Leu Phe Ala Gly Phe Ser Leu Ser Leu Val Ala
            500                 505                 510

Gln Ser Val Ser Ala Gln Glu Ala Lys Gln Pro Glu Lys Glu Glu Lys
            515                 520                 525

Asp Val Glu Val Ile Leu Val Ser Ala Gln Lys Arg Glu Gln Ala Leu
530                 535                 540

Lys Glu Val Pro Val Ser Ile Glu Val Ile Gln Gly Asp Leu Leu
545                 550                 555
```

(2) INFORMATION FOR SEQ ID NO: 3:

(i) SEQUENCE CHARACTERISTICS:
        (A) LENGTH: 1997 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (ix) FEATURE:
        (A) NAME/KEY: CDS

-continued (B) LOCATION:join(333..1805, 1866..1997)

(xi) SEQUENCE DESCRIPTION: SEQ ID NO: 3:

```
CCCTAAAAAC TATTCTTCAT ACCCTTTGAT GTATACGTTT AAACTATAGG GAGTTAATCT      60

GGTTTTGGTG CAATTCTAGT TTAATAAATG AAGCCTTCTT TTTTGACTTA CATTTTATTA     120

ACCTCTTGAA TTCTTGGGGC TTGCTAATTA TAAAATACTT AATATCAGGT GGTTGTGTAA     180

AAGAGGTGGA AGGGTATAGG ACCGTTACTT ATAATTGGCC CCTGTCGGAA GGGGGGTTAA     240

AGGTAAAATA GTGTTTAAGT GTATTAATTA ACTTCTATAT AAGTAGGAAA ATACACTATA     300

TATTGCGACA TTATTAACCT TAAATTCTTA CA ATG AAA TTA CAA TTT AAA CCT      353
                                   Met Lys Leu Gln Phe Lys Pro
                                    1               5
```

| | | | | | | | | | | | | | | | | |
|---|---|---|---|---|---|---|---|---|---|---|---|---|---|---|---|---|
|GTT|TAT|TTA|GCG|TCA|ATT|GCC|ATA|ATG|GCA|ATA|GGA|TGC|ACC|AAA|GAA|401|
|Val|Tyr|Leu|Ala|Ser|Ile|Ala|Ile|Met|Ala|Ile|Gly|Cys|Thr|Lys|Glu| |
| | |10| | | |15| | | |20| | | | | | |

| | | | | | | | | | | | | | | | | |
|---|---|---|---|---|---|---|---|---|---|---|---|---|---|---|---|---|
|GTG|ACG|GAA|AAC|GAT|ACC|TCC|GAA|ATT|TCG|GAA|GTT|CCA|ACT|GAA|TTG|449|
|Val|Thr|Glu|Asn|Asp|Thr|Ser|Glu|Ile|Ser|Glu|Val|Pro|Thr|Glu|Leu| |
| |25| | | |30| | | |35| | | | | | | |

| | | | | | | | | | | | | | | | | |
|---|---|---|---|---|---|---|---|---|---|---|---|---|---|---|---|---|
|AGG|GCC|GCG|GCT|TCT|TCA|TTT|TAT|ACC|CCA|CCG|GGT|CAG|AAT|GTA|CGG|497|
|Arg|Ala|Ala|Ala|Ser|Ser|Phe|Tyr|Thr|Pro|Pro|Gly|Gln|Asn|Val|Arg| |
|40| | | | |45| | | | |50| | | | |55| |

| | | | | | | | | | | | | | | | | |
|---|---|---|---|---|---|---|---|---|---|---|---|---|---|---|---|---|
|GCC|AAT|AAA|AAA|AAC|CTG|GTC|ACG|GAT|TAC|GGT|GTT|AAC|CAC|AAT|GAT|545|
|Ala|Asn|Lys|Lys|Asn|Leu|Val|Thr|Asp|Tyr|Gly|Val|Asn|His|Asn|Asp| |
| | | |60| | | |65| | | |70| | | | | |

| | | | | | | | | | | | | | | | | |
|---|---|---|---|---|---|---|---|---|---|---|---|---|---|---|---|---|
|CAG|AAC|GAT|GAT|AGT|AGC|AAA|TTA|AAC|CTG|GCT|ATC|AAA|GAT|TTA|TCG|593|
|Gln|Asn|Asp|Asp|Ser|Ser|Lys|Leu|Asn|Leu|Ala|Ile|Lys|Asp|Leu|Ser| |
| | |75| | | |80| | | |85| | | | | | |

| | | | | | | | | | | | | | | | | |
|---|---|---|---|---|---|---|---|---|---|---|---|---|---|---|---|---|
|GAT|ACC|GGT|GGT|ATA|CTG|ACC|CTT|CCT|AAG|GGA|AAG|TAC|TAT|TTG|ACC|641|
|Asp|Thr|Gly|Gly|Ile|Leu|Thr|Leu|Pro|Lys|Gly|Lys|Tyr|Tyr|Leu|Thr| |
| |90| | | |95| | | | |100| | | | | | |

| | | | | | | | | | | | | | | | | |
|---|---|---|---|---|---|---|---|---|---|---|---|---|---|---|---|---|
|AAA|ATT|AGA|ATG|CGC|TCT|AAT|GTA|CAT|CTT|GAA|ATA|GAA|AAG|GGA|ACG|689|
|Lys|Ile|Arg|Met|Arg|Ser|Asn|Val|His|Leu|Glu|Ile|Glu|Lys|Gly|Thr| |
|105| | | | |110| | | | |115| | | | | | |

| | | | | | | | | | | | | | | | | |
|---|---|---|---|---|---|---|---|---|---|---|---|---|---|---|---|---|
|GTA|ATC|TAT|CCG|ACC|AAG|GGG|TTG|ACT|CCT|GCG|AAG|AAT|CAC|AGA|ATT|737|
|Val|Ile|Tyr|Pro|Thr|Lys|Gly|Leu|Thr|Pro|Ala|Lys|Asn|His|Arg|Ile| |
|120| | | | |125| | | | |130| | | | |135| |

| | | | | | | | | | | | | | | | | |
|---|---|---|---|---|---|---|---|---|---|---|---|---|---|---|---|---|
|TTT|GAT|TTT|GCC|AGT|AAA|ACA|GAG|GAA|AAA|ATA|GAA|AAC|GCC|AGT|ATA|785|
|Phe|Asp|Phe|Ala|Ser|Lys|Thr|Glu|Glu|Lys|Ile|Glu|Asn|Ala|Ser|Ile| |
| | | |140| | | | |145| | | | |150| | | |

| | | | | | | | | | | | | | | | | |
|---|---|---|---|---|---|---|---|---|---|---|---|---|---|---|---|---|
|GTG|GGT|AAA|GGA|GGT|AAG|TTT|ATA|GTA|GAC|CTA|AGA|GGC|AAC|AGT|TCT|833|
|Val|Gly|Lys|Gly|Gly|Lys|Phe|Ile|Val|Asp|Leu|Arg|Gly|Asn|Ser|Ser| |
| | |155| | | | |160| | | | |165| | | | |

| | | | | | | | | | | | | | | | | |
|---|---|---|---|---|---|---|---|---|---|---|---|---|---|---|---|---|
|AAA|AAC|CAA|ATT|GTA|GCC|GAT|GTT|GGT|AAC|GTA|ACC|AAC|TTT|AAA|ATA|881|
|Lys|Asn|Gln|Ile|Val|Ala|Asp|Val|Gly|Asn|Val|Thr|Asn|Phe|Lys|Ile| |
| | | |170| | | |175| | | |180| | | | | |

| | | | | | | | | | | | | | | | | |
|---|---|---|---|---|---|---|---|---|---|---|---|---|---|---|---|---|
|TCG|AAT|TTT|ACG|ATC|AAG|GAT|GAA|AAA|ACC|ATC|TTT|GCT|TCG|ATA|TTG|929|
|Ser|Asn|Phe|Thr|Ile|Lys|Asp|Glu|Lys|Thr|Ile|Phe|Ala|Ser|Ile|Leu| |
| |185| | | |190| | | | |195| | | | | | |

| | | | | | | | | | | | | | | | | |
|---|---|---|---|---|---|---|---|---|---|---|---|---|---|---|---|---|
|GTA|AGC|TTT|ACG|GAT|AAG|GCA|GGC|AAT|GCT|TGG|CCA|CAT|AAA|GGT|ATT|977|
|Val|Ser|Phe|Thr|Asp|Lys|Ala|Gly|Asn|Ala|Trp|Pro|His|Lys|Gly|Ile| |
|200| | | | |205| | | | |210| | | | |215| |

| | | | | | | | | | | | | | | | | |
|---|---|---|---|---|---|---|---|---|---|---|---|---|---|---|---|---|
|ATT|GAG|AAT|ATA|GAC|CAG|GCG|AAT|GCC|CAT|ACG|GGA|TAT|GGC|CTC|ATA|1025|
|Ile|Glu|Asn|Ile|Asp|Gln|Ala|Asn|Ala|His|Thr|Gly|Tyr|Gly|Leu|Ile| |
| | | |220| | | | |225| | | | |230| | | |

| | | | | | | | | | | | | | | | | |
|---|---|---|---|---|---|---|---|---|---|---|---|---|---|---|---|---|
|CAG|GCG|TAC|GCG|GCA|GAT|AAC|ATT|CTG|TTC|AAC|AAT|CTA|AGT|TGT|ACG|1073|
|Gln|Ala|Tyr|Ala|Ala|Asp|Asn|Ile|Leu|Phe|Asn|Asn|Leu|Ser|Cys|Thr| |
| | |235| | | | |240| | | | |245| | | | |

| | | | | | | | | | | | | | | | | |
|---|---|---|---|---|---|---|---|---|---|---|---|---|---|---|---|---|
|GGC|GGG|GTA|ACC|TTG|CGT|TTA|GAA|ACC|GAC|AAC|CTC|GCT|ATG|AAA|ACC|1121|

```
                Gly Gly Val Thr Leu Arg Leu Glu Thr Asp Asn Leu Ala Met Lys Thr
                            250                 255                 260

GCT AAA AAA GGG GGT GTA AGG GAT ATT TTT GCC ACA AAG ATC AAG AAT         1169
Ala Lys Lys Gly Gly Val Arg Asp Ile Phe Ala Thr Lys Ile Lys Asn
            265                 270                 275

ACC AAT GGC TTG ACC CCG GTA ATG TTC TCT CCC CAT TTT ATG GAA AAC         1217
Thr Asn Gly Leu Thr Pro Val Met Phe Ser Pro His Phe Met Glu Asn
280                 285                 290                 295

GGT AAA GTG ACC ATA GAT GAT GTA ACC GCC ATC GGT TGT GCA TAT GCC         1265
Gly Lys Val Thr Ile Asp Asp Val Thr Ala Ile Gly Cys Ala Tyr Ala
                            300                 305                 310

GTA CGT GTA GAG CAC GGT TTT ATA GAG ATT TTC GAT AAG GGG AAT AGG         1313
Val Arg Val Glu His Gly Phe Ile Glu Ile Phe Asp Lys Gly Asn Arg
            315                 320                 325

GCA AGT GCC GAC GCT TTC AAG AAC TAT ATT GAA GGT ATT CTA GGA GCT         1361
Ala Ser Ala Asp Ala Phe Lys Asn Tyr Ile Glu Gly Ile Leu Gly Ala
            330                 335                 340

GGC TCG GTA GAA GTC GTG TAC AAA CGT AAT AAC GGA AGA ACA TGG GCG         1409
Gly Ser Val Glu Val Val Tyr Lys Arg Asn Asn Gly Arg Thr Trp Ala
            345                 350                 355

GCA CGT ATC GCA AAC GAC TTT AAC GAA GCG GCG TAT AAC CAC TCC AAT         1457
Ala Arg Ile Ala Asn Asp Phe Asn Glu Ala Ala Tyr Asn His Ser Asn
360                 365                 370                 375

CCT GCC GTT AGC GGA ATC AAA CCA GGG AAA TTC GCC ACA TCT AAG GTA         1505
Pro Ala Val Ser Gly Ile Lys Pro Gly Lys Phe Ala Thr Ser Lys Val
                            380                 385                 390

ACC AAT GTT AAG GCA ACC TAT AAG GGT ACT GGC GCC AAA CTC AAG CAG         1553
Thr Asn Val Lys Ala Thr Tyr Lys Gly Thr Gly Ala Lys Leu Lys Gln
            395                 400                 405

GCA TTC TTA TCC TAT TTA CCC TGT TCG GAA CGT TCT AAG GTT TGT CGG         1601
Ala Phe Leu Ser Tyr Leu Pro Cys Ser Glu Arg Ser Lys Val Cys Arg
            410                 415                 420

CCA GGT CCA GAT GGG TTC GAG TAT AAC GGA CCC TCC TTG GGA GTT ACC         1649
Pro Gly Pro Asp Gly Phe Glu Tyr Asn Gly Pro Ser Leu Gly Val Thr
425                 430                 435

ATC GAT AAC ACG AAA AGG GAC AAC AGC CTT GGC AAT TAT AAC GTC AAT         1697
Ile Asp Asn Thr Lys Arg Asp Asn Ser Leu Gly Asn Tyr Asn Val Asn
440                 445                 450                 455

GTA AGC ACC TCC AGT GTT CAG GGC TTT CCC AAT AAT TAC GTT TTA AAC         1745
Val Ser Thr Ser Ser Val Gln Gly Phe Pro Asn Asn Tyr Val Leu Asn
                            460                 465                 470

GTA AAG TAT AAT ACC CCT AAA GTA TGT AAC CAA AAT CTA GGT AGT ATT         1793
Val Lys Tyr Asn Thr Pro Lys Val Cys Asn Gln Asn Leu Gly Ser Ile
            475                 480                 485

ACT TCG TGT AAC TGATCACGAA ACAATTTGTA AATAAAAAGC AGCTGTCCCT             1845
Thr Ser Cys Asn
            490

TATTACGGGC GGCTGCTTTT ATG TCT TTA AGC CAT GTC GTG ATT TAT TGG           1895
                       Met Ser Leu Ser His Val Val Ile Tyr Trp
                                       495                 500

CGA CTT TTG ATA AAG GCT TGG ATT TCT TCC GGG GTA AAT ATC GGA TTG         1943
Arg Leu Leu Ile Lys Ala Trp Ile Ser Ser Gly Val Asn Ile Gly Leu
            505                 510                 515

GCC CCT TCC CTA CCG GCT ACC ATA GCT CTA TGC TCC TAT GCA CAG GCG         1991
Ala Pro Ser Leu Pro Ala Thr Ile Ala Leu Cys Ser Tyr Ala Gln Ala
            520                 525                 530

AAA TCT                                                                 1997
Lys Ser
    535
```

(2) INFORMATION FOR SEQ ID NO: 4:

(i) SEQUENCE CHARACTERISTICS:
        (A) LENGTH: 535 amino acids
        (B) TYPE: amino acid
        (D) TOPOLOGY: linear (ii) MOLECULE TYPE: protein (xi) SEQUENCE DESCRIPTION: SEQ ID NO: 4:

```
Met Lys Leu Gln Phe Lys Pro Val Tyr Leu Ala Ser Ile Ala Ile Met
 1               5                  10                  15

Ala Ile Gly Cys Thr Lys Glu Val Thr Glu Asn Asp Thr Ser Glu Ile
            20                  25                  30

Ser Glu Val Pro Thr Glu Leu Arg Ala Ala Ser Ser Phe Tyr Thr
            35                  40                  45

Pro Pro Gly Gln Asn Val Arg Ala Asn Lys Lys Asn Leu Val Thr Asp
        50                  55                  60

Tyr Gly Val Asn His Asn Asp Gln Asn Asp Asp Ser Ser Lys Leu Asn
 65                  70                  75                  80

Leu Ala Ile Lys Asp Leu Ser Asp Thr Gly Gly Ile Leu Thr Leu Pro
                85                  90                  95

Lys Gly Lys Tyr Tyr Leu Thr Lys Ile Arg Met Arg Ser Asn Val His
                100                 105                 110

Leu Glu Ile Glu Lys Gly Thr Val Ile Tyr Pro Thr Lys Gly Leu Thr
            115                 120                 125

Pro Ala Lys Asn His Arg Ile Phe Asp Phe Ala Ser Lys Thr Glu Glu
        130                 135                 140

Lys Ile Glu Asn Ala Ser Ile Val Gly Lys Gly Gly Lys Phe Ile Val
145                 150                 155                 160

Asp Leu Arg Gly Asn Ser Ser Lys Asn Gln Ile Val Ala Asp Val Gly
                165                 170                 175

Asn Val Thr Asn Phe Lys Ile Ser Asn Phe Thr Ile Lys Asp Glu Lys
            180                 185                 190

Thr Ile Phe Ala Ser Ile Leu Val Ser Phe Thr Asp Lys Ala Gly Asn
        195                 200                 205

Ala Trp Pro His Lys Gly Ile Ile Glu Asn Ile Asp Gln Ala Asn Ala
210                 215                 220

His Thr Gly Tyr Gly Leu Ile Gln Ala Tyr Ala Ala Asp Asn Ile Leu
225                 230                 235                 240

Phe Asn Asn Leu Ser Cys Thr Gly Gly Val Thr Leu Arg Leu Glu Thr
                245                 250                 255

Asp Asn Leu Ala Met Lys Thr Ala Lys Lys Gly Gly Val Arg Asp Ile
            260                 265                 270

Phe Ala Thr Lys Ile Lys Asn Thr Asn Gly Leu Thr Pro Val Met Phe
        275                 280                 285

Ser Pro His Phe Met Glu Asn Gly Lys Val Thr Ile Asp Asp Val Thr
    290                 295                 300

Ala Ile Gly Cys Ala Tyr Ala Val Arg Val Glu His Gly Phe Ile Glu
305                 310                 315                 320

Ile Phe Asp Lys Gly Asn Arg Ala Ser Ala Asp Ala Phe Lys Asn Tyr
                325                 330                 335

Ile Glu Gly Ile Leu Gly Ala Gly Ser Val Glu Val Val Tyr Lys Arg
            340                 345                 350

Asn Asn Gly Arg Thr Trp Ala Ala Arg Ile Ala Asn Asp Phe Asn Glu
```

```
                355                 360                 365
Ala Ala Tyr Asn His Ser Asn Pro Ala Val Ser Gly Ile Lys Pro Gly
    370                 375                 380

Lys Phe Ala Thr Ser Lys Val Thr Asn Val Lys Ala Thr Tyr Lys Gly
385                 390                 395                 400

Thr Gly Ala Lys Leu Lys Gln Ala Phe Leu Ser Tyr Leu Pro Cys Ser
                405                 410                 415

Glu Arg Ser Lys Val Cys Arg Pro Gly Pro Asp Gly Phe Glu Tyr Asn
                420                 425                 430

Gly Pro Ser Leu Gly Val Thr Ile Asp Asn Thr Lys Arg Asp Asn Ser
                435                 440                 445

Leu Gly Asn Tyr Asn Val Asn Val Ser Thr Ser Ser Val Gln Gly Phe
    450                 455                 460

Pro Asn Asn Tyr Val Leu Asn Val Lys Tyr Asn Thr Pro Lys Val Cys
465                 470                 475                 480

Asn Gln Asn Leu Gly Ser Ile Thr Ser Cys Asn Met Ser Leu Ser His
                485                 490                 495

Val Val Ile Tyr Trp Arg Leu Leu Ile Lys Ala Trp Ile Ser Ser Gly
                500                 505                 510

Val Asn Ile Gly Leu Ala Pro Ser Leu Pro Ala Thr Ile Ala Leu Cys
                515                 520                 525

Ser Tyr Ala Gln Ala Lys Ser
                530                 535

(2) INFORMATION FOR SEQ ID NO: 5:

(i) SEQUENCE CHARACTERISTICS:
        (A) LENGTH: 2180 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (ix) FEATURE:
        (A) NAME/KEY: CDS
        (B) LOCATION:join(1..498, 741..1931, 2009..2179)

(xi) SEQUENCE DESCRIPTION: SEQ ID NO: 5:

GAT CAT ATC ATT CCT TTG CAA ATT AAA AAT TCT CAA GAT AGT CAA ATA        48
Asp His Ile Ile Pro Leu Gln Ile Lys Asn Ser Gln Asp Ser Gln Ile
1               5                   10                  15

ATT AGT TTT TTT AAA GCT GAC AAA GGG AGT GTG AGC AGG CAA GTA CAC        96
Ile Ser Phe Phe Lys Ala Asp Lys Gly Ser Val Ser Arg Gln Val His
                20                  25                  30

CCA CCT TGG CCT GTG CCT TGT AAA AGT AAA CTG CAA GAG CAA GAT AGT       144
Pro Pro Trp Pro Val Pro Cys Lys Ser Lys Leu Gln Glu Gln Asp Ser
            35                  40                  45

AGT GAG TCT AAA GAG AGT AAG GCA GAG CAA GTT AAA ATT AAC AAC TGC       192
Ser Glu Ser Lys Glu Ser Lys Ala Glu Gln Val Lys Ile Asn Asn Cys
    50                  55                  60

GTT GTA CAG AAC GCA ATG CTG TAC ATA GAA AAC AAT TAT TTC AAC GAT       240
Val Val Gln Asn Ala Met Leu Tyr Ile Glu Asn Asn Tyr Phe Asn Asp
65                  70                  75                  80

ATA AAT ATA GAC ACG GTT GCT TTT TCT GTT GGC GTA AGT CGC TCT TAT       288
Ile Asn Ile Asp Thr Val Ala Phe Ser Val Gly Val Ser Arg Ser Tyr
                85                  90                  95

CTC GTT AAA CAA TTT AAG TTA GCA ACG AAT AAA ACG ATT AAT AAT AGA       336
```

-continued

| | | |
|---|---|---|
| Leu Val Lys Gln Phe Lys Leu Ala Thr Asn Lys Thr Ile Asn Asn Arg<br>100 105 110 | | |
| ATC ATA GAA GTA AGA ATA GAG CAG GCT AAA AAA GTA TTA CTA AAA AAA<br>Ile Ile Glu Val Arg Ile Glu Gln Ala Lys Lys Val Leu Leu Lys Lys<br>115 120 125 | 384 | |
| TCT GTT ACA GAA ACA GCT TAT GAA GTT GGT TTT AAT AAC TCA AAC TAC<br>Ser Val Thr Glu Thr Ala Tyr Glu Val Gly Phe Asn Asn Ser Asn Tyr<br>130 135 140 | 432 | |
| TTC GCG ACA GTT TTT AAA AAA AGA ACA AAC TAC ACG CCC AAG CAA TTT<br>Phe Ala Thr Val Phe Lys Lys Arg Thr Asn Tyr Thr Pro Lys Gln Phe<br>145 150 155 160 | 480 | |
| AAA CGT ACT TTT TCC AGC TAAAACTACA ACTAAATAAC GATTAAAAGC<br>Lys Arg Thr Phe Ser Ser<br>165 | 528 | |
| CATTTTTAGA GAACAGTAAA ACCATTTTTT GAGGTTTGGT GTTGTATATA AATATTAAAT | 588 | |
| ATCCCCACTC GCTCAGCTTT TTTTGTGCGA GTTGTGAGAA TTAGCTTAAC AGGTAAGGTT | 648 | |
| TACGTATCTG TATATCTAAA CTCTTCGAAT ATAACACTGT ATCTGTTGCT GAGCTGTGGC | 708 | |
| TCAGTTCACA CTAACAAAGG ATGGATAAAT AA ATG AAA CCT ATA AGT ATT GTG<br>Met Lys Pro Ile Ser Ile Val<br>170 | 761 | |
| GCA TTC CCT ATA CCA GCT ATA AGT ATG CTT CTT TTA AGT GCA GTA TCA<br>Ala Phe Pro Ile Pro Ala Ile Ser Met Leu Leu Leu Ser Ala Val Ser<br>175 180 185 | 809 | |
| CAA GCA GCA TCT ATG CAA CCT CCC ATC GCA AAA CCT GGT GAA ACA TGG<br>Gln Ala Ala Ser Met Gln Pro Pro Ile Ala Lys Pro Gly Glu Thr Trp<br>190 195 200 205 | 857 | |
| ATT TTA CAA GCC AAA CGC TCT GAC GAA TTT AAC GTA AAA GAT GCG ACA<br>Ile Leu Gln Ala Lys Arg Ser Asp Glu Phe Asn Val Lys Asp Ala Thr<br>210 215 220 | 905 | |
| AAG TGG AAC TTT CAA ACA GAA AAC TAT GGG GTA TGG TCT TGG AAA AAT<br>Lys Trp Asn Phe Gln Thr Glu Asn Tyr Gly Val Trp Ser Trp Lys Asn<br>225 230 235 | 953 | |
| GAA AAT GCG ACA GTA TCT AAT GGC AAA CTA AAA TTA ACC ACT AAG CGA<br>Glu Asn Ala Thr Val Ser Asn Gly Lys Leu Lys Leu Thr Thr Lys Arg<br>240 245 250 | 1001 | |
| GAA TCT CAT CAA CGT ACA TTC TGG GAT GGC TGT AAT CAG CAG CAA GTT<br>Glu Ser His Gln Arg Thr Phe Trp Asp Gly Cys Asn Gln Gln Gln Val<br>255 260 265 | 1049 | |
| GCA AAT TAC CCA CTT TAT TAT ACA TCG GGT GTC GCT AAA TCC AGA GCT<br>Ala Asn Tyr Pro Leu Tyr Tyr Thr Ser Gly Val Ala Lys Ser Arg Ala<br>270 275 280 285 | 1097 | |
| ACA GGT AAT TAT GGC TAT TAC GAA GCT CGA ATC AAA GGA GCG AGT ACA<br>Thr Gly Asn Tyr Gly Tyr Tyr Glu Ala Arg Ile Lys Gly Ala Ser Thr<br>290 295 300 | 1145 | |
| TTT CCT GGC GTA TCG CCT GCT TTT TGG ATG TAT AGC ACC ATT GAC CGT<br>Phe Pro Gly Val Ser Pro Ala Phe Trp Met Tyr Ser Thr Ile Asp Arg<br>305 310 315 | 1193 | |
| TCA TTA ACG AAA GAA GGG GAT GTC CAA TAT AGC GAA ATA GAC GTA GTG<br>Ser Leu Thr Lys Glu Gly Asp Val Gln Tyr Ser Glu Ile Asp Val Val<br>320 325 330 | 1241 | |
| GAA CTT ACT CAA AAA AGT GCA GTG AGA GAG TCT GAT CAT GAC TTA CAC<br>Glu Leu Thr Gln Lys Ser Ala Val Arg Glu Ser Asp His Asp Leu His<br>335 340 345 | 1289 | |
| AAT ATT GTA GTA AAA AAT GGA AAA CCA ACA TGG ATG CGT CCA GGG TCT<br>Asn Ile Val Val Lys Asn Gly Lys Pro Thr Trp Met Arg Pro Gly Ser<br>350 355 360 365 | 1337 | |
| TTT CCG CAG ACA AAT CAT AAC GGA TAC CAT CTA CCT TTC GAT CCT CGA<br>Phe Pro Gln Thr Asn His Asn Gly Tyr His Leu Pro Phe Asp Pro Arg | 1385 | |

```
                      370             375             380
AAT GAC TTT CAC ACC TAT GGT GTC AAT GTA ACT AAA GAC AAG ATC ACT     1433
Asn Asp Phe His Thr Tyr Gly Val Asn Val Thr Lys Asp Lys Ile Thr
            385                 390                 395

TGG TAC GTA GAT GGT GAA ATT GTG GGC GAA AAG GAT AAC TTA TAC TGG     1481
Trp Tyr Val Asp Gly Glu Ile Val Gly Glu Lys Asp Asn Leu Tyr Trp
            400                 405                 410

CAT CGT CAA ATG AAT CTC ACA TTA TCA CAA GGC TTA CGC GCG CCG CAT     1529
His Arg Gln Met Asn Leu Thr Leu Ser Gln Gly Leu Arg Ala Pro His
        415                 420                 425

ACA CAA TGG AAA TGT AAT CAA TTT TAC CCA TCA GCG AAT AAA TCA GCA     1577
Thr Gln Trp Lys Cys Asn Gln Phe Tyr Pro Ser Ala Asn Lys Ser Ala
430                 435                 440                 445

GAA GGC TTC CCA ACA TCA ATG GAA GTT GAT TAT GTA AGA ACG TGG GTA     1625
Glu Gly Phe Pro Thr Ser Met Glu Val Asp Tyr Val Arg Thr Trp Val
                450                 455                 460

AAG GTG GGC AAT AAC AAC TCT GCT CCA GGC GAG GGG CAG TCA TGT CCT     1673
Lys Val Gly Asn Asn Asn Ser Ala Pro Gly Glu Gly Gln Ser Cys Pro
            465                 470                 475

AAC ACG TTT GTA GCT GTC AAT AGT GTT CAA CTA AGC GCA GCA AAA CAA     1721
Asn Thr Phe Val Ala Val Asn Ser Val Gln Leu Ser Ala Ala Lys Gln
            480                 485                 490

ACA CTT CGA AAG GGC CAA TCT ACA ACG CTA GAA AGC ACA GTT CTT CCA     1769
Thr Leu Arg Lys Gly Gln Ser Thr Thr Leu Glu Ser Thr Val Leu Pro
        495                 500                 505

AAC TGT GCA ACC AAC AAG AAA GTC ATT TAT TCA TCA AGC AAT AAA AAT     1817
Asn Cys Ala Thr Asn Lys Lys Val Ile Tyr Ser Ser Ser Asn Lys Asn
510                 515                 520                 525

GTG GCA ACT GTG AAC AGT GCT GGC GTT GTA AAA GCT AAA AAT AAA GGC     1865
Val Ala Thr Val Asn Ser Ala Gly Val Val Lys Ala Lys Asn Lys Gly
                530                 535                 540

ACT GCG ACG ATT ACG GTT AAA ACT AAA AAC AAA GGG AAA ATA GAT AAA     1913
Thr Ala Thr Ile Thr Val Lys Thr Lys Asn Lys Gly Lys Ile Asp Lys
            545                 550                 555

TTA ACC ATT GCG GTG AAT TAAGCTAACT CAAACTAGCC TCGAAGGATT           1961
Leu Thr Ile Ala Val Asn
            560

GAGGCACTTT ATTTATAGGT CTCAGGCTTC GACTTTTTGG AGGGGGT ATG AAA AAG    2017
                                                    Met Lys Lys
                                                        565

GTA AAT TTA TCC AGC AAG TGG ATA ATT AGC ATT AGT TTA CTA ATC ATT    2065
Val Asn Leu Ser Ser Lys Trp Ile Ile Ser Ile Ser Leu Leu Ile Ile
            570                 575                 580

TGT GAT TAT GTT TAT TTA ATA CGA ACA AAC GTT AAC GAG CAA GCT AAC    2113
Cys Asp Tyr Val Tyr Leu Ile Arg Thr Asn Val Asn Glu Gln Ala Asn
            585                 590                 595

GCA GAA GCT ACT GCA CAT ATG CAT TAC AAA ATA AAT AAT ACG AAA CAC    2161
Ala Glu Ala Thr Ala His Met His Tyr Lys Ile Asn Asn Thr Lys His
600                 605                 610

TCA AAA GGA AAG CTT GAT C                                          2180
Ser Lys Gly Lys Leu Asp
615             620

(2) INFORMATION FOR SEQ ID NO: 6:

(i) SEQUENCE CHARACTERISTICS:
        (A) LENGTH: 620 amino acids
        (B) TYPE: amino acid
        (D) TOPOLOGY: linear (ii) MOLECULE TYPE: protein
```

(xi) SEQUENCE DESCRIPTION: SEQ ID NO: 6:

```
Asp His Ile Ile Pro Leu Gln Ile Lys Asn Ser Gln Asp Ser Gln Ile
  1               5                  10                  15

Ile Ser Phe Phe Lys Ala Asp Lys Gly Ser Val Ser Arg Gln Val His
             20                  25                  30

Pro Pro Trp Pro Val Pro Cys Lys Ser Lys Leu Gln Glu Gln Asp Ser
         35                  40                  45

Ser Glu Ser Lys Glu Ser Lys Ala Glu Gln Val Lys Ile Asn Asn Cys
 50                  55                  60

Val Val Gln Asn Ala Met Leu Tyr Ile Glu Asn Asn Tyr Phe Asn Asp
 65                  70                  75                  80

Ile Asn Ile Asp Thr Val Ala Phe Ser Val Gly Val Ser Arg Ser Tyr
                 85                  90                  95

Leu Val Lys Gln Phe Lys Leu Ala Thr Asn Lys Thr Ile Asn Asn Arg
                100                 105                 110

Ile Ile Glu Val Arg Ile Glu Gln Ala Lys Lys Val Leu Leu Lys Lys
            115                 120                 125

Ser Val Thr Glu Thr Ala Tyr Glu Val Gly Phe Asn Asn Ser Asn Tyr
130                 135                 140

Phe Ala Thr Val Phe Lys Lys Arg Thr Asn Tyr Thr Pro Lys Gln Phe
145                 150                 155                 160

Lys Arg Thr Phe Ser Ser Met Lys Pro Ile Ser Ile Val Ala Phe Pro
                165                 170                 175

Ile Pro Ala Ile Ser Met Leu Leu Ser Ala Val Ser Gln Ala Ala
                180                 185                 190

Ser Met Gln Pro Pro Ile Ala Lys Pro Gly Glu Thr Trp Ile Leu Gln
            195                 200                 205

Ala Lys Arg Ser Asp Glu Phe Asn Val Lys Asp Ala Thr Lys Trp Asn
210                 215                 220

Phe Gln Thr Glu Asn Tyr Gly Val Trp Ser Trp Lys Asn Glu Asn Ala
225                 230                 235                 240

Thr Val Ser Asn Gly Lys Leu Lys Leu Thr Thr Lys Arg Glu Ser His
                245                 250                 255

Gln Arg Thr Phe Trp Asp Gly Cys Asn Gln Gln Gln Val Ala Asn Tyr
            260                 265                 270

Pro Leu Tyr Tyr Thr Ser Gly Val Ala Lys Ser Arg Ala Thr Gly Asn
275                 280                 285

Tyr Gly Tyr Tyr Glu Ala Arg Ile Lys Gly Ala Ser Thr Phe Pro Gly
290                 295                 300

Val Ser Pro Ala Phe Trp Met Tyr Ser Thr Ile Asp Arg Ser Leu Thr
305                 310                 315                 320

Lys Glu Gly Asp Val Gln Tyr Ser Glu Ile Asp Val Val Glu Leu Thr
                325                 330                 335

Gln Lys Ser Ala Val Arg Glu Ser Asp His Asp Leu His Asn Ile Val
            340                 345                 350

Val Lys Asn Gly Lys Pro Thr Trp Met Arg Pro Gly Ser Phe Pro Gln
            355                 360                 365

Thr Asn His Asn Gly Tyr His Leu Pro Phe Asp Pro Arg Asn Asp Phe
370                 375                 380

His Thr Tyr Gly Val Asn Val Thr Lys Asp Lys Ile Thr Trp Tyr Val
385                 390                 395                 400

Asp Gly Glu Ile Val Gly Glu Lys Asp Asn Leu Tyr Trp His Arg Gln
```

```
                    405                 410                 415
Met Asn Leu Thr Leu Ser Gln Gly Leu Arg Ala Pro His Thr Gln Trp
            420                 425                 430

Lys Cys Asn Gln Phe Tyr Pro Ser Ala Asn Lys Ser Ala Glu Gly Phe
            435                 440                 445

Pro Thr Ser Met Glu Val Asp Tyr Val Arg Thr Trp Val Lys Val Gly
            450                 455                 460

Asn Asn Asn Ser Ala Pro Gly Glu Gly Gln Ser Cys Pro Asn Thr Phe
465                 470                 475                 480

Val Ala Val Asn Ser Val Gln Leu Ser Ala Ala Lys Gln Thr Leu Arg
                485                 490                 495

Lys Gly Gln Ser Thr Thr Leu Glu Ser Thr Val Leu Pro Asn Cys Ala
            500                 505                 510

Thr Asn Lys Lys Val Ile Tyr Ser Ser Ser Asn Lys Asn Val Ala Thr
            515                 520                 525

Val Asn Ser Ala Gly Val Val Lys Ala Lys Asn Lys Gly Thr Ala Thr
            530                 535                 540

Ile Thr Val Lys Thr Lys Asn Lys Gly Lys Ile Asp Lys Leu Thr Ile
545                 550                 555                 560

Ala Val Asn Met Lys Lys Val Asn Leu Ser Ser Lys Trp Ile Ile Ser
                565                 570                 575

Ile Ser Leu Leu Ile Ile Cys Asp Tyr Val Tyr Leu Ile Arg Thr Asn
            580                 585                 590

Val Asn Glu Gln Ala Asn Ala Glu Ala Thr Ala His Met His Tyr Lys
            595                 600                 605

Ile Asn Asn Thr Lys His Ser Lys Gly Lys Leu Asp
610                 615                 620

(2) INFORMATION FOR SEQ ID NO: 7:

(i) SEQUENCE CHARACTERISTICS:
        (A) LENGTH: 2600 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (ix) FEATURE:
        (A) NAME/KEY: CDS
        (B) LOCATION:875..2509

(xi) SEQUENCE DESCRIPTION: SEQ ID NO: 7:

GCCTCCGTAT TCGACAATGT TGTACGATGC TTGGCGATTC GGACTCTGTT TAAGCACTCG       60

ATTTCGTAAA GGCACTATCC ACTCATTCAT TCCGACTCAA TATTCTTTTC GACAAATGCA      120

ACCGGTTCCA TTGAAAAGGC CCTAAAAATA CAGCTTTCCC GCCCCCCATC GTAGAAGGTT      180

CCAATATGCT TCAACCCCTT TTTCAGCCTT ACTTCAGGGG TATTACTTTC ATGCCTAGGG      240

CCGCAAATAC ATTCGCTTGG ACCCAGTCAC CTATATAATT GAATACGGAA CTACCCATGG      300

CTTCCTTCCC TTTGGGAACC TATGGTACAG ACTTGCCTTT TTAAACCGG TTACTTCAGC       360

TAATTCGCCA AGCTGGTTCC TTCATAACCT TTGGCCCGAA ACACCTTGCA AGCACATAAA      420

TCTTATCCAA TATTTTGCGG TCTCATGGGA CAAATCTATA ACAAACATTC AATTTTACCA      480

AACGTTCGGT AATAAATCTA GTCAAAAACG GGTCCGATT CATTTTAGAA GAAAGGTAAA      540

GCCCCCAAAA GAGCGGTTTA CTTGAAGATA TGATTTATAA AACACAATAA GTGACAAAGG      600
```

-continued

```
AAGATCATGG CTATAATTAG TTGAAAAAAC AGGGCTTACC ATGACATGGA GCTTTATTGA    660

AAACAGATGT CCAACAAGAA TAAAGGAGGG CCGTTCGACC GCGACGTTTA AATAAAAACA    720

TATTCCATAT CAAAATTTAA TTAAGGTTCT TTCCTACAGT ATTTATAAGA AATTACTAAA    780

ATTAGTTAGG ATAATACTAC AAAATGGTAA AATTGGATTA CTCAGATTGA ACCATAGCCT    840

CTACTTTAGT CGGCTAACAA AAACAATTAT AGTA ATG AAA AAA CCA AAT TTT        892
                                      Met Lys Lys Pro Asn Phe
                                       1                5

TAT GGC AAG ATG GGT AGA ACT GCA CTT TCA AGT CTT TTC TAC CTC TTT      940
Tyr Gly Lys Met Gly Arg Thr Ala Leu Ser Ser Leu Phe Tyr Leu Phe
             10                 15                  20

TTC CTA GGC CTT GTG TAT GGG CAA CAA CCT ACG AAG ACT TCA AAT CCG      988
Phe Leu Gly Leu Val Tyr Gly Gln Gln Pro Thr Lys Thr Ser Asn Pro
         25                  30                  35

AAC GAT CAG TGG ACC ATC AAA TGG AGT GCT TCG GAC GAA TTC AAC AAA     1036
Asn Asp Gln Trp Thr Ile Lys Trp Ser Ala Ser Asp Glu Phe Asn Lys
     40                  45                  50

AAT GAC CCC GAC TGG GCA AAA TGG ATC AAG ACA GGA AAC CTT CCG AAT     1084
Asn Asp Pro Asp Trp Ala Lys Trp Ile Lys Thr Gly Asn Leu Pro Asn
 55                  60                  65                  70

ACA TCG GCA TGG AAA TGG AAC AAT CAA AAA AAC GTA AAG ATT TCC AAC     1132
Thr Ser Ala Trp Lys Trp Asn Asn Gln Lys Asn Val Lys Ile Ser Asn
                 75                  80                  85

GGA ATT GCG GAA CTA ACG ATG AGG CAT AAC GCC AAT AAT ACC CCA CCT     1180
Gly Ile Ala Glu Leu Thr Met Arg His Asn Ala Asn Asn Thr Pro Pro
                     90                  95                 100

GAC GGA GGA ACC TAT TTC ACC TCT GGG ATA TTT AAG TCG TAC CAA AAA     1228
Asp Gly Gly Thr Tyr Phe Thr Ser Gly Ile Phe Lys Ser Tyr Gln Lys
                105                 110                 115

TTT ACG TAT GGA TAC TTT GAG GCC AAA ATC CAA GGA GCG GAT ATA GGT     1276
Phe Thr Tyr Gly Tyr Phe Glu Ala Lys Ile Gln Gly Ala Asp Ile Gly
    120                 125                 130

GAA GGC GTA TGC CCA TCG TTT TGG CTT TAT AGT GAT TTC GAC TAT TCC     1324
Glu Gly Val Cys Pro Ser Phe Trp Leu Tyr Ser Asp Phe Asp Tyr Ser
135                 140                 145                 150

GTA GCC AAT GGG GAA ACG GTA TAC AGT GAA ATA GAT GTA GTT GAA CTA     1372
Val Ala Asn Gly Glu Thr Val Tyr Ser Glu Ile Asp Val Val Glu Leu
                155                 160                 165

CAA CAA TTC GAT TGG TAT GAA GGC CAT CAG GAC GAC ATT TAC GAC ATG     1420
Gln Gln Phe Asp Trp Tyr Glu Gly His Gln Asp Asp Ile Tyr Asp Met
                    170                 175                 180

GAC TTA AAT CTA CAC GCC GTT GTC AAA GAA AAC GGA CAG GGG GTT TGG     1468
Asp Leu Asn Leu His Ala Val Val Lys Glu Asn Gly Gln Gly Val Trp
                185                 190                 195

AAA AGG CCA AAA ATG TAC CCT CAA GAA CAG TTG AAC AAA TGG AGA GCC     1516
Lys Arg Pro Lys Met Tyr Pro Gln Glu Gln Leu Asn Lys Trp Arg Ala
200                 205                 210

ATG GAC CCG AGT AAA GAC TTT CAT ATC TAT GGT TGT GAA GTG AAC CAG     1564
Met Asp Pro Ser Lys Asp Phe His Ile Tyr Gly Cys Glu Val Asn Gln
215                 220                 225                 230

AAC GAA ATC ATA TGG TAT GTT GAC GGT GTC GAG GTT GCC CGA AAA CCA     1612
Asn Glu Ile Ile Trp Tyr Val Asp Gly Val Glu Val Ala Arg Lys Pro
                235                 240                 245

AAT AAA TAT TGG CAT CGC CCC ATG AAC GTT ACC CTT TCA TTG GGA CTC     1660
Asn Lys Tyr Trp His Arg Pro Met Asn Val Thr Leu Ser Leu Gly Leu
                250                 255                 260

AGA AAA CCA TTT GTG AAA TTT TTC GAC AAT AAG AAC AAT GCC ATA AAT     1708
Arg Lys Pro Phe Val Lys Phe Phe Asp Asn Lys Asn Asn Ala Ile Asn
```

-continued

```
            265               270               275
CCA GAA ACC GAT GCC AAG GCA AGG GAA AAA TTA TCG GAT ATA CCT ACA    1756
Pro Glu Thr Asp Ala Lys Ala Arg Glu Lys Leu Ser Asp Ile Pro Thr
        280               285               290

TCG ATG TAT GTG GAT TAC GTT CGG GTC TGG GAA AAA TCA GCA GGT AAC    1804
Ser Met Tyr Val Asp Tyr Val Arg Val Trp Glu Lys Ser Ala Gly Asn
295               300               305               310

ACT ACC AAT CCC CCA ACC AGC GAG GTC GGC ACA CTA AAA ACA AAG GGT    1852
Thr Thr Asn Pro Pro Thr Ser Glu Val Gly Thr Leu Lys Thr Lys Gly
            315               320               325

TCG AAA CTG GTG ATT GAC CAT TGG GAT GCA AGT ACA GGG ACT ATT TCG    1900
Ser Lys Leu Val Ile Asp His Trp Asp Ala Ser Thr Gly Thr Ile Ser
        330               335               340

GCT GTC AGT AAC AAT ACA AAG ACA GGT CAA TAT GCC GGT TCA GTG AAC    1948
Ala Val Ser Asn Asn Thr Lys Thr Gly Gln Tyr Ala Gly Ser Val Asn
    345               350               355

AAC GCG AGC ATC GCC CAG ATA GTA ACA TTA AAA GCG AAT ACT TCA TAT    1996
Asn Ala Ser Ile Ala Gln Ile Val Thr Leu Lys Ala Asn Thr Ser Tyr
360               365               370

AAG GTA TCG GCT TTC GGA AAG GCC AGC TCA CCC GGA ACA TCG GCT TAT    2044
Lys Val Ser Ala Phe Gly Lys Ala Ser Ser Pro Gly Thr Ser Ala Tyr
375               380               385               390

CTA GGC ATT AGT AAA GCA TCC AAC AAC GAA CTC ATA AGC AAT TTT GAA    2092
Leu Gly Ile Ser Lys Ala Ser Asn Asn Glu Leu Ile Ser Asn Phe Glu
            395               400               405

TTC AAA ACA ACC TCA TAC TCC AAA GGC GAG ATT GAG ATA AGA ACT GGA    2140
Phe Lys Thr Thr Ser Tyr Ser Lys Gly Glu Ile Glu Ile Arg Thr Gly
        410               415               420

AAT GTT CAG GAA TCA TAT CGC ATA TGG TAT TGG TCT TCC GGG CAA GCC    2188
Asn Val Gln Glu Ser Tyr Arg Ile Trp Tyr Trp Ser Ser Gly Gln Ala
    425               430               435

TAT TGC GAT GAT TTT AAC CTT GTT GAA ATA AAC AGC GGG GCT TCA CAA    2236
Tyr Cys Asp Asp Phe Asn Leu Val Glu Ile Asn Ser Gly Ala Ser Gln
440               445               450

CTC AAT GAA AAT GAG ACT GAA ACA GCA CTG GAA AAA GGT ATA CAC ATT    2284
Leu Asn Glu Asn Glu Thr Glu Thr Ala Leu Glu Lys Gly Ile His Ile
455               460               465               470

TAT CCG AAT CCC TAT AAA AAC GGT CCA TTG ACA ATC GAT TTT GGC AAA    2332
Tyr Pro Asn Pro Tyr Lys Asn Gly Pro Leu Thr Ile Asp Phe Gly Lys
            475               480               485

CCC TTC AGC GGC GAG GTC CAA ATC ACC GGT TTA AAC GGT AGA ACA TTC    2380
Pro Phe Ser Gly Glu Val Gln Ile Thr Gly Leu Asn Gly Arg Thr Phe
        490               495               500

TTA AGA AGA AAT GTT GTC GAT CAA ACT TCG GTT CAG CTC CTA GAA TCC    2428
Leu Arg Arg Asn Val Val Asp Gln Thr Ser Val Gln Leu Leu Glu Ser
    505               510               515

AAA TCT AAA TTC AAG AGC GGT CTA TAT ATC GTT AAA ATT AGT GGC CCG    2476
Lys Ser Lys Phe Lys Ser Gly Leu Tyr Ile Val Lys Ile Ser Gly Pro
520               525               530

GAT GGA GAG GTT TCA AAA AAG ATA CTC GTG GAG TAACTAAAAA TCAATTTTTA  2529
Asp Gly Glu Val Ser Lys Lys Ile Leu Val Glu
535               540               545

CAGGATTACA GACGGGCAAA GGGATTTTCC TTTGCCCGTT TTTAAAATTA TGGGCGGAAA  2589

CGATTGTTGC G                                                       2600
```

(2) INFORMATION FOR SEQ ID NO: 8:

(i) SEQUENCE CHARACTERISTICS:
        (A) LENGTH: 545 amino acids

-continued (B) TYPE: amino acid
(D) TOPOLOGY: linear (ii) MOLECULE TYPE: protein (xi) SEQUENCE DESCRIPTION: SEQ ID NO: 8:

```
Met Lys Lys Pro Asn Phe Tyr Gly Lys Met Gly Arg Thr Ala Leu Ser
  1               5                  10                  15

Ser Leu Phe Tyr Leu Phe Phe Leu Gly Leu Val Tyr Gly Gln Gln Pro
                 20                  25                  30

Thr Lys Thr Ser Asn Pro Asn Asp Gln Trp Thr Ile Lys Trp Ser Ala
             35                  40                  45

Ser Asp Glu Phe Asn Lys Asn Asp Pro Asp Trp Ala Lys Trp Ile Lys
 50                  55                  60

Thr Gly Asn Leu Pro Asn Thr Ser Ala Trp Lys Trp Asn Asn Gln Lys
 65                  70                  75                  80

Asn Val Lys Ile Ser Asn Gly Ile Ala Glu Leu Thr Met Arg His Asn
                 85                  90                  95

Ala Asn Asn Thr Pro Pro Asp Gly Gly Thr Tyr Phe Thr Ser Gly Ile
                100                 105                 110

Phe Lys Ser Tyr Gln Lys Phe Thr Tyr Gly Tyr Phe Glu Ala Lys Ile
                115                 120                 125

Gln Gly Ala Asp Ile Gly Glu Gly Val Cys Pro Ser Phe Trp Leu Tyr
130                 135                 140

Ser Asp Phe Asp Tyr Ser Val Ala Asn Gly Glu Thr Val Tyr Ser Glu
145                 150                 155                 160

Ile Asp Val Val Glu Leu Gln Gln Phe Asp Trp Tyr Glu Gly His Gln
                165                 170                 175

Asp Asp Ile Tyr Asp Met Asp Leu Asn Leu His Ala Val Val Lys Glu
                180                 185                 190

Asn Gly Gln Gly Val Trp Lys Arg Pro Lys Met Tyr Pro Gln Glu Gln
                195                 200                 205

Leu Asn Lys Trp Arg Ala Met Asp Pro Ser Lys Asp Phe His Ile Tyr
210                 215                 220

Gly Cys Glu Val Asn Gln Asn Glu Ile Ile Trp Tyr Val Asp Gly Val
225                 230                 235                 240

Glu Val Ala Arg Lys Pro Asn Lys Tyr Trp His Arg Pro Met Asn Val
                245                 250                 255

Thr Leu Ser Leu Gly Leu Arg Lys Pro Phe Val Lys Phe Phe Asp Asn
                260                 265                 270

Lys Asn Asn Ala Ile Asn Pro Glu Thr Asp Ala Lys Ala Arg Glu Lys
                275                 280                 285

Leu Ser Asp Ile Pro Thr Ser Met Tyr Val Asp Tyr Val Arg Val Trp
290                 295                 300

Glu Lys Ser Ala Gly Asn Thr Thr Asn Pro Pro Thr Ser Glu Val Gly
305                 310                 315                 320

Thr Leu Lys Thr Lys Gly Ser Lys Leu Val Ile Asp His Trp Asp Ala
                325                 330                 335

Ser Thr Gly Thr Ile Ser Ala Val Ser Asn Asn Thr Lys Thr Gly Gln
                340                 345                 350

Tyr Ala Gly Ser Val Asn Asn Ala Ser Ile Ala Gln Ile Val Thr Leu
                355                 360                 365

Lys Ala Asn Thr Ser Tyr Lys Val Ser Ala Phe Gly Lys Ala Ser Ser
370                 375                 380
```

```
-continued

Pro Gly Thr Ser Ala Tyr Leu Gly Ile Ser Lys Ala Ser Asn Asn Glu
385                 390                 395                 400

Leu Ile Ser Asn Phe Glu Phe Lys Thr Thr Ser Tyr Ser Lys Gly Glu
                405                 410                 415

Ile Glu Ile Arg Thr Gly Asn Val Gln Glu Ser Tyr Arg Ile Trp Tyr
            420                 425                 430

Trp Ser Ser Gly Gln Ala Tyr Cys Asp Asp Phe Asn Leu Val Glu Ile
        435                 440                 445

Asn Ser Gly Ala Ser Gln Leu Asn Glu Asn Glu Thr Glu Thr Ala Leu
    450                 455                 460

Glu Lys Gly Ile His Ile Tyr Pro Asn Pro Tyr Lys Asn Gly Pro Leu
465                 470                 475                 480

Thr Ile Asp Phe Gly Lys Pro Phe Ser Gly Glu Val Gln Ile Thr Gly
                485                 490                 495

Leu Asn Gly Arg Thr Phe Leu Arg Arg Asn Val Val Asp Gln Thr Ser
            500                 505                 510

Val Gln Leu Leu Glu Ser Lys Ser Lys Phe Lys Ser Gly Leu Tyr Ile
        515                 520                 525

Val Lys Ile Ser Gly Pro Asp Gly Glu Val Ser Lys Lys Ile Leu Val
    530                 535                 540

Glu
545
```